United States Patent
Ago et al.

(10) Patent No.: US 11,830,179 B2
(45) Date of Patent: Nov. 28, 2023

(54) FOOD INSPECTION ASSISTING SYSTEM, FOOD INSPECTION ASSISTING APPARATUS AND COMPUTER PROGRAM

(71) Applicant: NICHIREI FOODS INC., Tokyo-to (JP)

(72) Inventors: Yusuke Ago, Chiba (JP); Shinya Tsukamoto, Chiba (JP); Minoru Mamiya, Chiba (JP)

(73) Assignee: NICHIREI FOODS INC., Tokyo (JP)

(*) Notice: Subject to any disclaimer, the term of this patent is extended or adjusted under 35 U.S.C. 154(b) by 0 days.

(21) Appl. No.: 16/966,177

(22) PCT Filed: Jan. 31, 2019

(86) PCT No.: PCT/JP2019/003366
§ 371 (c)(1),
(2) Date: Jul. 30, 2020

(87) PCT Pub. No.: WO2019/151394
PCT Pub. Date: Aug. 8, 2019

(65) Prior Publication Data
US 2021/0035276 A1    Feb. 4, 2021

(30) Foreign Application Priority Data
Jan. 31, 2018   (JP) ................. 2018-015921

(51) Int. Cl.
*G06T 7/70*        (2017.01)
*G01N 33/02*      (2006.01)
(Continued)

(52) U.S. Cl.
CPC ......... *G06T 7/001* (2013.01); *G01N 21/8851* (2013.01); *G01N 33/02* (2013.01);
(Continued)

(58) Field of Classification Search
CPC .. G06T 7/001; G06T 7/62; G06T 7/70; G06T 7/90; G06T 2207/10024;
(Continued)

(56) References Cited

U.S. PATENT DOCUMENTS 4,631,413 A * 12/1986 Jensen ............... G01N 21/6486
250/910
7,460,227 B1    12/2008 Kim et al.
(Continued)

FOREIGN PATENT DOCUMENTS

JP          60-40939 A    3/1985
JP          10-48141 A    2/1998
(Continued)

OTHER PUBLICATIONS

International Search Report, issued in PCT/JP2019/003366, PCT/ISA/210, dated Apr. 9, 2019.
(Continued)

*Primary Examiner* — Siamak Harandi
(74) *Attorney, Agent, or Firm* — Birch, Stewart, Kolasch & Birch, LLP

(57) ABSTRACT

The present embodiment provides a food inspection assisting system, a food inspection assisting apparatus and a computer program for accurately and rapidly inspecting food. According to one embodiment, a food inspection assisting system includes a carrying apparatus, a sensing apparatus, an assisting information generator, an information output apparatus and a controller. The carrying apparatus carries a food item. The sensing apparatus senses the food item carried. The assisting information generator generates inspection assisting information for the food item based on output information of the sensing apparatus. The information output apparatus that displays the inspection assisting information. The controller controls timing to
(Continued)

display the inspection assisting information based on time required to carry the food item to an inspection area in which the carried food item is inspected.

19 Claims, 19 Drawing Sheets

(51) Int. Cl.
    *G06T 7/00*         (2017.01)
    *G06T 7/62*         (2017.01)
    *G06T 7/90*         (2017.01)
    *G01N 21/88*      (2006.01)
    *G06F 3/14*        (2006.01)

(52) U.S. Cl.
    CPC ............... *G06F 3/14* (2013.01); *G06T 7/62* (2017.01); *G06T 7/70* (2017.01); *G06T 7/90* (2017.01); *G01N 2021/8893* (2013.01); *G06T 2207/10024* (2013.01); *G06T 2207/10048* (2013.01); *G06T 2207/30128* (2013.01)

(58) Field of Classification Search
    CPC . G06T 2207/10048; G06T 2207/30128; G06T 2207/10016; G01N 21/8851; G01N 33/02; G01N 2021/8893; G01N 21/9515; G01N 2021/845; G06F 3/14
    See application file for complete search history.

(56) References Cited

U.S. PATENT DOCUMENTS

| | | | |
|---|---|---|---|
| 7,976,368 | B2 | 7/2011 | Haucke et al. |
| 2006/0156878 | A1 | 7/2006 | Faires et al. |
| 2007/0058777 | A1 | 3/2007 | Kondo |
| 2007/0238147 | A1 | 10/2007 | Okamoto et al. |
| 2009/0080706 | A1* | 3/2009 | Tao ............ G06T 7/0004 382/110 |
| 2010/0002835 | A1* | 1/2010 | Kabumoto ........... G01N 23/04 378/207 |
| 2010/0029187 | A1 | 2/2010 | Haucke et al. |
| 2012/0145911 | A1* | 6/2012 | Suyama .............. G01V 5/0041 250/366 |

FOREIGN PATENT DOCUMENTS

| | | |
|---|---|---|
| JP | 2002-228593 A | 8/2002 |
| JP | 2005-233636 A | 9/2005 |
| JP | 2006-177890 A | 7/2006 |
| JP | 2007-286041 A | 11/2007 |
| JP | 2009-115613 A | 5/2009 |
| JP | 2010-505397 A | 2/2010 |
| JP | 2010-227892 A | 10/2010 |
| JP | 2012-7952 A | 1/2012 |
| JP | 2014-109526 A | 6/2014 |
| JP | 2016-90476 A | 5/2016 |
| JP | 2017-133953 A | 8/2017 |
| JP | 2017-142133 A | 8/2017 |
| JP | 2017-211325 A | 11/2017 |
| JP | 2017-215264 A | 12/2017 |
| WO | WO 95/21375 A1 | 8/1995 |
| WO | WO 2005/043149 A1 | 5/2005 |
| WO | WO 2008/102148 A1 | 8/2008 |
| WO | WO 2014/079448 A1 | 5/2014 |
| WO | WO 2017/174768 A1 | 10/2017 |

OTHER PUBLICATIONS

Written Opinion of the International Searching Authority, issued in PCT/JP2019/003366, PCT/ISA/237, dated Apr. 9, 2019.
International Preliminary on Patentability and English translation of the Written Opinion of the International Searching Authority for International Applicatication No. PCT/JP2019/003366, dated Aug. 13, 2020.
Japanese Notice of Reasons for Refusal for Japanese Application No. 2022-192930, dated Jun. 27, 2023, with an English translation.
"Overview of Japan's Poultry Meat Inspection Laws and How to Respond to Them", Journal of the Poultry Science Society of Japan, vol. 28, No. 6, 1991, pp. 340-352 (39 pages total), with an English translation.

* cited by examiner

RED 131

GREEN 132

NEAR INFRARED 134

BLUE 133

FOOD INSPECTION ASSISTING SYSTEM, FOOD INSPECTION ASSISTING APPARATUS AND COMPUTER PROGRAM

CROSS REFERENCE TO RELATED APPLICATIONS

This application is based upon and claims the benefit of priority from the prior Japanese Patent Application No. 2018-015921, filed on Jan. 31, 2018, the entire contents of which are incorporated herein by reference.

FIELD

Embodiments of the present invention relate to a food inspection assisting system, a food inspection assisting apparatus and a computer program.

BACKGROUND

In the process of food production, removal of foreign matter and defects from raw materials is performed in an operation of screening the raw materials before being processed. For example, in the production of processed foods containing chicken, removal of foreign matter such as bones and feathers and defects such as blood-containing part is performed in the operation of screening the raw materials. It is desired to reduce operational errors and speed up the screening operation. However, increasing the number of workers incurs high production cost.

In the process of food production, introduction of apparatuses for assisting accurate inspection, such as an X-ray inspection apparatus, has been proceeding. In the screening operation using the X-ray inspection apparatus, if, for example, the mixing of a bone in a raw material is found in an X-ray image, a worker compares the X-ray image and the raw material while searching for the bone by visual check or palpation, and removes the bone found. However, this has problems in efficiency and accuracy, such as that it may take time to find the position of the bone and that the bone may be overlooked. Besides bones, feathers and blood-containing part also need to be removed, and also need to be detected accurately and efficiently.

PRIOR ART DOCUMENT

[Patent Document 1] Japanese Patent Publication NO. 2017-142133
[Patent Document 2] Japanese Patent Publication NO. 2007-286041
[Patent Document 3] Japanese Patent Publication NO. 2005-233636

Problem to be Solved

The present embodiment provides a food inspection assisting system, a food inspection assisting apparatus and a computer program for accurately and rapidly inspecting food.

SUMMARY

According to one embodiment, a food inspection assisting system includes a carrying apparatus, a sensing apparatus, an assisting information generator, an information output apparatus and a controller. The carrying apparatus carries a food item. The sensing apparatus senses the food item carried. The assisting information generator generates inspection assisting information for the food item based on output information of the sensing apparatus. The information output apparatus that displays the inspection assisting information. The controller controls timing to display the inspection assisting information based on time required to carry the food item to an inspection area in which the carried food item is inspected.

DETAILED DESCRIPTION

Figure 1:
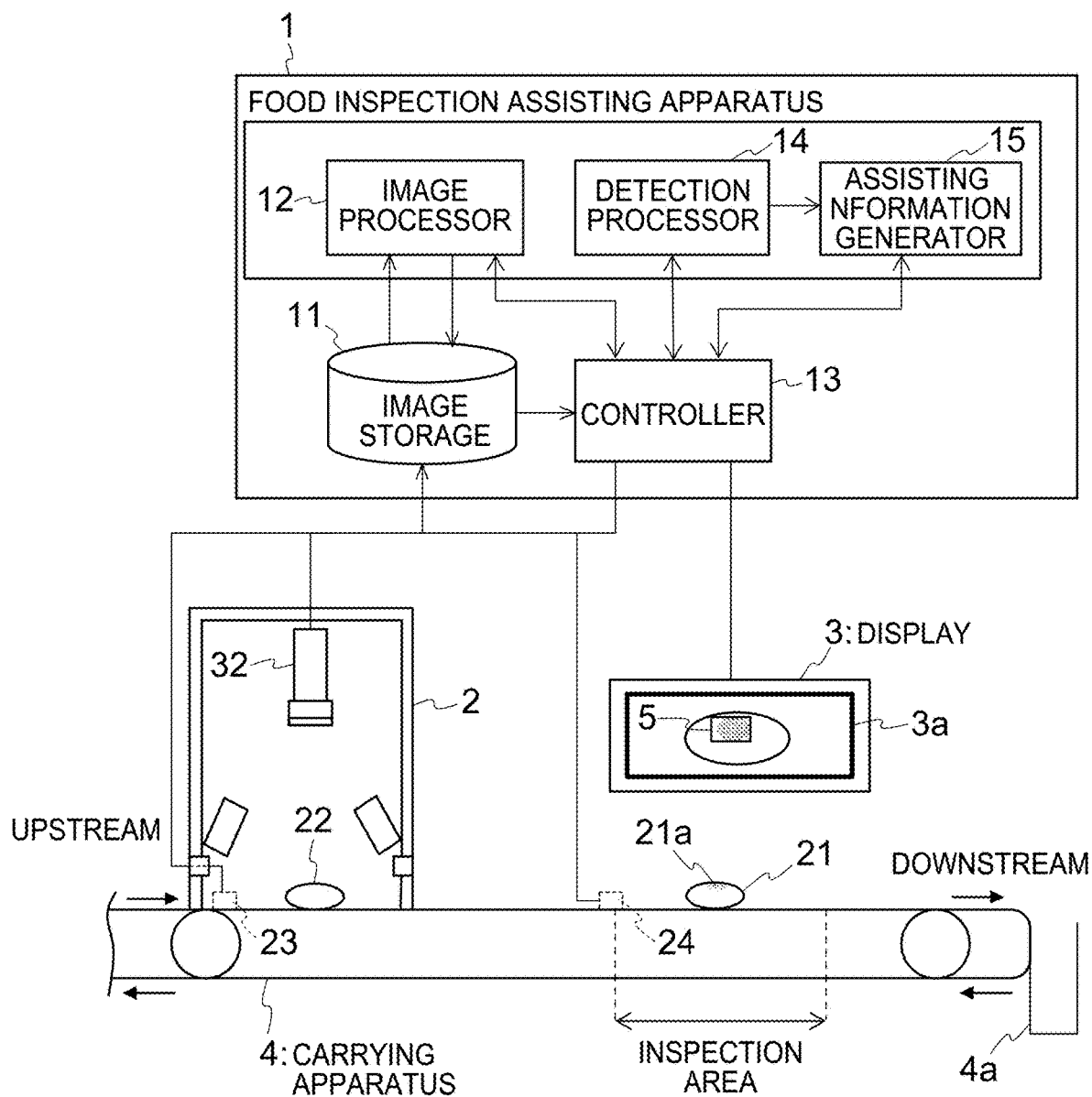
FIG. 1 shows an example of a food inspection assisting system according to a first embodiment.

The following describes embodiments of the present invention with reference to the drawings. In the drawings, the same components are provided with the same reference numerals, and the descriptions thereof may be omitted.

First Embodiment

FIG. 1 shows a configuration example of a food inspection assisting system (hereinafter "system") according to a first embodiment. The system of FIG. 1 includes a food inspection assisting apparatus (hereinafter "inspection assisting apparatus") 1, an image capturing apparatus 2 that is a sensing apparatus, a display 3 that is an information output apparatus, and a carrying apparatus 4.

In the system of FIG. 1, a food item that is to be inspected (target food item) is carried by the carrying apparatus 4 in the right direction along the paper plane at a constant speed. The side from which the food item is carried is referred to as the upstream side, and the side toward which the food item is carried is referred to as the downstream side. On the upstream side, food items are placed on the carrying apparatus 4 manually by a worker or by a machine at constant time intervals or at arbitrary time intervals. When a sensor 23 detects that a food item enters an image-capturing region in the housing of the image capturing apparatus 2, a camera 32 captures an image of the food item. The figure illustrates a situation in which an image of a food item 22 is captured. For each food item, the number of times of image capture may be one, or a plurality of times of continuous image capture may be performed (for example, ten times for one second). In the case of continuous image capture, the food item moves in the carrying channel even during the image capture, so that captured images are obtained in which the position of the food item gradually changes in the image-capturing region.

The captured images as output information of the image capturing apparatus 2 are sent to the inspection assisting apparatus 1, and the inspection assisting apparatus 1 performs processing of detecting foreign matter or a defect based on the captured images. Specifically, after performing various types of image processing on the captured images, processing of detecting foreign matter or a defect is performed based on the processed image. Note that a food item containing foreign matter or a defect may be referred to as a defective item, and a food item containing no foreign matter or defect may be referred to as a quality item.

Examples of the food item to be inspected include chicken, pork, beef, mutton, seafoods, vegetables, fruits, grains, beverages and seasonings, and the type of the food item is not particularly limited. In cases of meat such as chicken, pork, beef and seafood, the object to be inspected may be unheated raw meat or may be heated meat. The food item may be an unprocessed raw material, may be a raw cut of meat, or may have been subjected to some processing. That is, the degree to which the food item has been processed is also not particularly limited.

The first embodiment is described using an example in which a raw cut of chicken is used as an object to be inspected and a feather is to be detected as foreign matter. The object to be detected as foreign matter may be other than a feather (for example, a bone, a cartilage, a wood piece, feedstuff and the like).

When foreign matter (a feather) is detected in an image, the system identifies the position of the feather, and generates inspection assisting information including information representing the identified position. An example of the information representing the identified position is data indicating the identified position. In the present embodiment, frame data (for example, rectangle frame data) enclosing the detected feather is generated as such data. The system arranges the generated frame data on the captured image. In this manner, an image is generated in which the feather included in the captured image is enclosed by the frame data. The image is used as the inspection assisting information. The data indicating the identified position is not limited to frame data, and may be data of an arrow indicating the identified position or may be other forms of data.

In the system, an inspection area in which the food item is inspected is provided on the downstream side relative to the image capturing apparatus 2 along the carrying channel of the carrying apparatus 4. A display 3 is arranged near the inspection area. The display 3 is an example of an information output apparatus that displays information to the worker. Another example of the information output apparatus is a projection apparatus that projects information. Examples of the projection apparatus include a projector that projects information by light, a beam projector that projects information by light beams, and the like. Embodiments using a projector and a beam projector will be described later.

The display 3 is provided at a position such that a worker can see a screen 3a of the display 3 when the worker performs inspection in the inspection area. For example, if the worker is positioned on the near side with respect to the paper plane in the figure, the display 3 is provided on the deeper side with respect to the paper plane across the carrying apparatus 4 such that the screen is directed to the worker.

The worker inspects the food item carried to (appearing in) the inspection area. As an example, the inspection is performed by visual check or palpation, or by both. The inspection assisting apparatus 1 displays the inspection assisting information on the display 3 in accordance with the timing when the food item is carried to the inspection area, that is, the timing when the food item appears in the inspection area. In other words, the inspection assisting information is not displayed until the food item appears in the inspection area. From the worker's point of view, the inspection assisting information is displayed on the display 3 in synchronization with the appearance of the food item in the inspection area. In the figure, an image in which foreign matter (a feather) is enclosed by frame data 5 is displayed on the display 3.

The worker inspects the food item being carried while looking at the displayed inspection assisting information. Specifically, the worker knows the position of the feather based on the frame data 5, searches the portion corresponding to the frame data 5 and nearby portions for the feather, and removes the feather found. For example, the worker discards the removed feather in a predetermined case. Because the food item gradually moves in front of the worker during the inspection, the worker needs to efficiently remove the feather. In the present embodiment, the worker can quickly identify the position of the feather and can efficiently remove the feather by referring to the inspection assisting information displayed on the display 3.

The system may continue displaying the inspection assisting information while the food item is in the inspection area, or may display the inspection assisting information for a predetermined period of time after the food item enters the inspection area. If a plurality of times of image capture (continuous image capture) of the food item is performed, the system may continuously (for example, at constant time intervals) display a plurality of pieces of inspection assisting information generated for the plurality of captured images during the period between when the food item enters and exits the inspection area. In this manner, the inspection assisting information can be seen as a moving image synchronized with the food item being carried. The frame data 5 included in the inspection assisting information displayed on the display 3 appears to move in accordance with the movement of the food item. Thus, the worker can more efficiently search for the feather.

The following describes the components of the system of FIG. 1 in detail.

The carrying apparatus 4 is an apparatus that carries a food item provided on the upstream side by a worker, a machine or the like toward the downstream side. Various conveyor apparatuses such as a belt conveyor, a chain conveyor, a roller conveyor, a mesh conveyor, a gravity conveyor and the like can be used as the carrying apparatus 4. The conveyor apparatus is an example, and other carrying means may be used to carry the food item. Note that, while FIG. 1 shows an example in which the food item is carried from the left to the right, the direction of carrying the food item is not particularly limited.

At the entrance of the inspection area of the carrying apparatus 4, a sensor 24 is arranged on one or both sides of the carrying channel. The sensor 24 detects the passage of the food item. Specifically, the sensor 24 detects that the food item is carried to the inspection area. When detecting the passage of the food item, the sensor 24 outputs a detection signal to a controller 13. Examples of the sensor 24 include a laser sensor, an infrared sensor, an ultrasonic sensor, various photoelectric sensors, an image sensor, a weight sensor and the like, and the type of the sensor is not particularly limited.

A collecting apparatus 4a is arranged downstream from the inspection area in the carrying apparatus 4. The collecting apparatus 4a collects food items that have been inspected. The carrying apparatus 4 may be electrically connected to the food inspection assisting apparatus 1 so that the carrying apparatus 4 is controlled from the food inspection assisting apparatus 1. For example, the carrying speed, the turning on and off of the operation and the like may be controlled. While in the present embodiment, the carrying apparatus 4 carries the food item at a constant speed, the worker may adjust the turning on and off and the speed by operating an operating unit provided on the carrying apparatus 4. Note that the food item may also be carried to the next step (e.g., a cooking step) instead of being collected in the collecting apparatus 4a.

The image capturing apparatus 2 captures an image of the food item carried to an image-capturing region inside its housing while illuminating the food item by a light source. Data of the image captured by the image capturing apparatus 2 is sent to the inspection assisting apparatus 1, and is saved in an image storage 11. As an interface between the image capturing apparatus 2 and the inspection assisting apparatus 1, Ethernet, wireless LAN, PCI Express, USB, UART, SPI, SDIO, serial port, Bluetooth (registered trademark) and the like can be used. These interfaces are examples, and it is not intended to prohibit the use of other manners.

Figure 2:
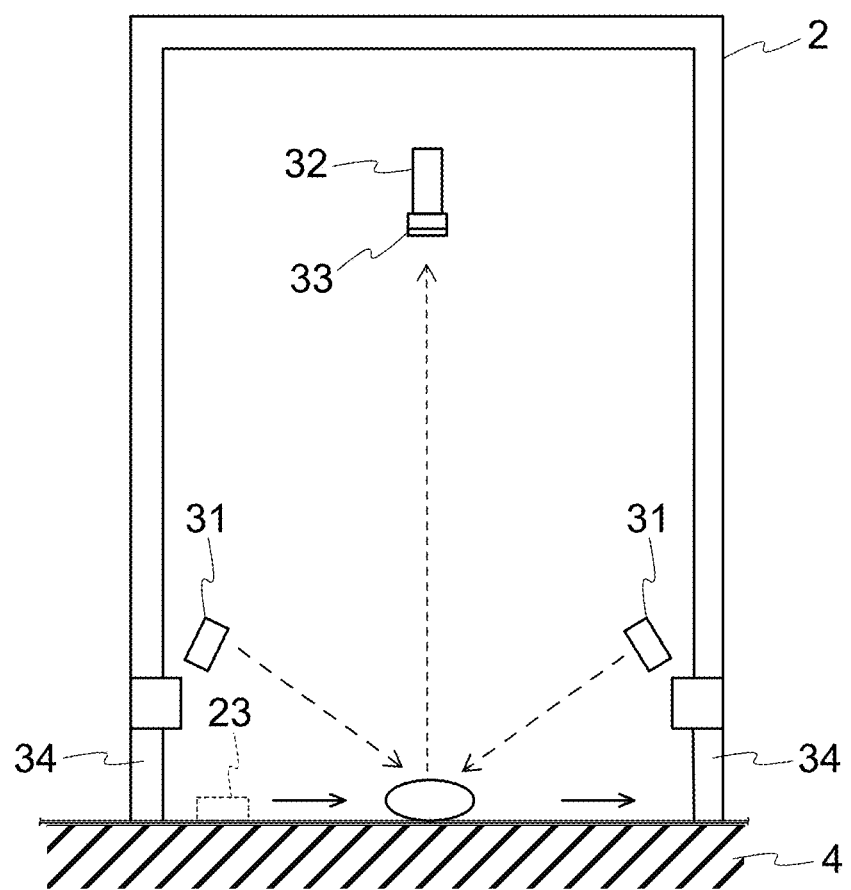
FIG. 2 is a cross-sectional view of an image capturing apparatus according to the first embodiment.

FIG. 2 is a cross-sectional view of the image capturing apparatus 2. The image capturing apparatus 2 includes one or more lighting units 31, a camera 32, a filter 33 and a sensor 23. The image capturing apparatus 2 has a housing with a substantially cuboidal shape, and an opening 34 for passing the food item is formed in the bottom part of the housing facing the carrying apparatus 4. The image capturing apparatus 2 covers a partial area of the carrying apparatus 4 from above. A wall is formed on some or all of the side surfaces of the housing. Also, a ceiling is formed on the top of the housing. The ceiling and wall can reduce the entrance of infrared light, visible light and the like from external light sources into the image-capturing region. In this manner, the image capturing apparatus 2 can selectively project light from a desired light source onto the food item that is the subject of image capture.

Note that the image capturing apparatus 2 may lack one or both of the ceiling and the wall. For example, if the image capturing apparatus 2 is provided in a darkroom, effects from external light sources are not significant, and the ceiling and wall for blocking light can be omitted. Examples of the materials of the ceiling and wall include stainless steel, aluminum, resin and the like, and the material is not particularly limited. While in the example of the figure, the image capture is performed from directly above the carrying channel, the image capture may be performed from obliquely above or in a plurality of directions.

The one or more lighting units 31 are provided in a lower part of the housing of the image capturing apparatus 2. The lighting units 31 are apparatuses that emit ultraviolet light. The irradiation of the chicken feather with ultraviolet light causes fluorescence to occur, which enables the detection of the feather. The lighting units 31 irradiate the image-capturing region below the image capturing apparatus 2 with ultraviolet light. In the example of the figure, two lighting units 31 are provided. As an example, the two lighting units 31 have a cuboidal shape extending in the direction vertical to the paper plane. However, their shape is not limited to the above. For example, the shape of the lighting units 31 may be cylindrical. Alternatively, there may be a single lighting unit 31 formed in a ring shape.

Examples of the light source in the lighting unit 31 include an ultraviolet LED, a black light, various florescent lamps and the like, and the type of the light source is not particularly limited. In the case of detecting a chicken feather, an ultraviolet light source having a spectral peak wavelength within the range from 365 nm to 400 nm is preferably used as the light source. As an example, an ultraviolet light source having a spectral peak wavelength of 375 nm can be used. However, the spectrum of the light source is not particularly limited. A light source containing visible light components besides ultraviolet components may also be used.

The type of the light source used may be determined according to the type of the food item to be inspected, the type of the foreign matter or defect to be detected, and the like. For example, in the case of detecting a bone (or cartilage) as foreign matter, X-rays can be used. In general, when a substance is irradiated with electromagnetic waves, the resulting reaction varies with the type of the substance. For example, different substances have different wavelengths (frequencies) of electromagnetic waves to absorb, reflect, and emit florescence. Thus, fluorescence spectral analysis may be performed on the food item to be inspected and the foreign matter or defect to be detected, to determine the wavelengths of electromagnetic waves that evoke strong reaction. For example, a fluorescence spectrophotometer can be used to perform the fluorescence spectral analysis.

The camera 32 captures an image of the food item irradiated with ultraviolet light emitted from the lighting unit 31. The camera 32 is provided with, for example, a CMOS image sensor or a CCD image sensor mounted therein, and can obtain a color image including color information relating to the food item that is the subject of image capture. These image sensors are examples, and the image capture may be performed using different devices. The camera 32 may have a fixed-focus lens or a zoom lens, and the type of the lens is not particularly limited. An example of the resolution of an image captured by the camera 32 is full HD (1920×1080 pixels), and the resolution of the captured image is not particularly limited.

A filter 33 is provided on the front side of the camera 32. The camera 32 detects, through the filter 33, fluorescence emitted from the food item irradiated with ultraviolet light from the lighting unit 31. The filter 33 is provided to allow easy discrimination of foreign matter using the image captured by the camera 32. In the case of detecting a chicken feather as foreign matter, the use of a green filter as the filter 33 allows easy detection of the feather. That is, a portion containing the feather clearly appears and can easily be discriminated from other portions of the chicken. The green filter is a filter that passes wavelengths in the wavelength range of green (for example, electromagnetic waves near a wavelength of 520 nm) and blocks other wavelength ranges. The present embodiment assumes the case of using a green filter as the filter 33 for performing detection of a feather as foreign matter.

Figure 3A:
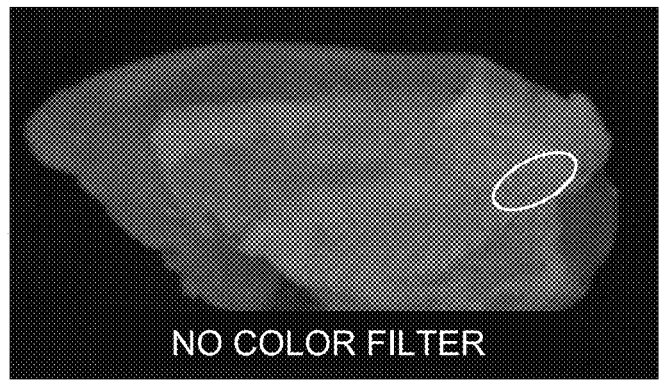
FIGS. 3A to 3C show an example of an image obtained without color filters, an image obtained through a blue filter and an image obtained through a green filter.
Figure 3B:
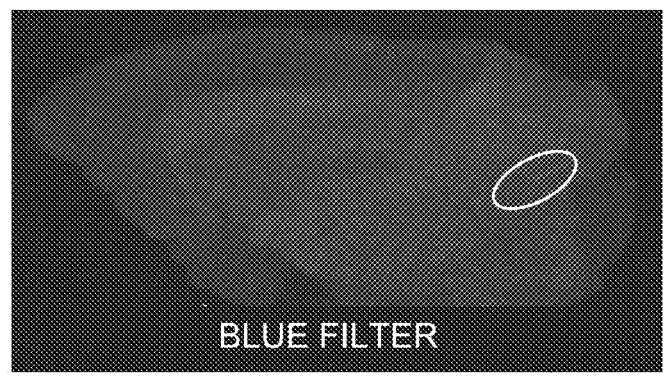
Figure 3C:
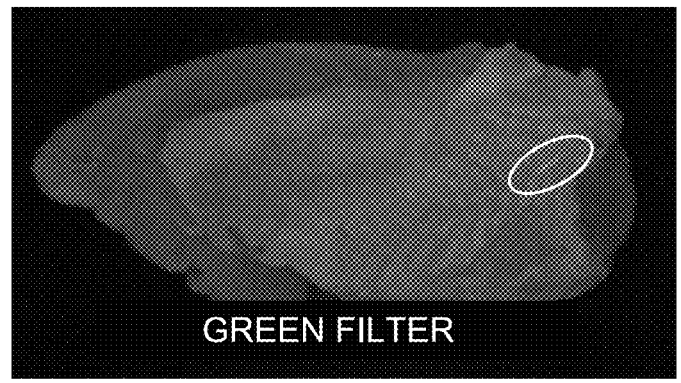

FIG. 3A shows an example of an image of chicken captured without a color filter. The region enclosed by an oval in FIG. 3A contains a part of a feather. Referring to FIG. 3A, slightly light-colored lines are included in the portion containing the feather, but are unclear. FIG. 3B shows an example of an image obtained through a blue filter. In FIG. 3B as well, the region enclosed by a white oval contains a part of a feather. Although portions around the feather have low luminance, the portion containing the feather also has reduced luminance, and the feather is blurred. FIG. 3C shows an example of an image captured through a green filter. The region enclosed by a white oval contains a feather. In the image in FIG. 3C, the portion containing the feather clearly appears and can easily be discriminated from other portions of the chicken. In light of these results, it will be understood that performing the image capture through the green filter allows easy discrimination of the feather.

The sensor 23 detects that the food item is carried into the housing of the image capturing apparatus 2 by the carrying apparatus 4. Specifically, the sensor 23 detects that the food item enters the image-capturing region of the image capturing apparatus 2. The sensor 23 is arranged at a different position than the food item being carried in the direction vertical to the paper plane so as not to obstruct the passage of the food item. Examples of the sensor 23 include a laser sensor, an infrared sensor, an ultrasonic sensor, various photoelectric sensors, an image sensor, a weight sensor and the like, and the type of the sensor is not particularly limited.

The display 3 is an information output apparatus that displays information such as an image or a text on the screen 3*a*. The display 3 is in wired or wireless connection with the inspection assisting apparatus 1. As an interface between the inspection assisting apparatus 1 and the display 3, wireless LAN, PCI Express, USB, UART, SPI, SDIO, serial port, Bluetooth, Ethernet and the like can be used. These interfaces are examples, and other manners may also be used. As the display 3, for example, an LCD (liquid crystal display), a CRT (cathode-ray tube), an organic EL (organic electroluminescent) display and the like can be used, and other types of devices may also be used. The display 3 is arranged at a position and in an orientation such that the worker performing the inspection can see the screen 3*a* during the inspection. For example, the screen 3*a* of the display 3 may be positioned in front of, obliquely above, obliquely left to, obliquely right to or obliquely below the worker across the carrying apparatus 4.

The inspection assisting apparatus 1 performs image processing on an image captured by the image capturing apparatus 2, processing of detecting foreign matter or a defect, processing of generating inspection assisting information including information identifying the position of the detected foreign matter or defect, timing control of displaying the inspection assisting information to the worker, and the like. As an example, the inspection assisting apparatus 1 is an information processing apparatus such as a computing machine provided with one or more CPUs (central processing units), a storage and a communication unit and capable of running an OS (operating system) and applications. Some or all of the functions of the inspection assisting apparatus 1 may be achieved by semiconductor circuits such as an FPGA and an ASIC or a GPU (Graphics Processing Unit). The inspection assisting apparatus 1 may be a physical computing machine, or may be implemented by a virtual machine (VM), a container or combinations thereof. The functions of the inspection assisting apparatus 1 may be distributed among one or more physical computing machines, virtual machines and containers. It is also not prohibited to use configurations having an increased number of inspection assisting apparatuses 1 for purposes of improving availability and load distribution.

The inspection assisting apparatus 1 includes an image storage 11, an image processor 12, a controller 13, a detection processor 14 and an assisting information generator 15.

When the controller 13 receives a detection signal from the sensor 23 of the image capturing apparatus 2, the controller 13 sends a signal for instruction of image capture to the camera 32 of the image capturing apparatus 2. That is, the controller 13 instructs the camera 32 to perform image capture at the timing when the food item enters an image-capturing angle range (image-capturing region) of the camera 32. In this manner, automatic image capture of the carried food item is performed.

The image storage 11 has a storage space to save images captured by the camera 32 of the image capturing apparatus 2. The image storage 11 may be a volatile memory such as an SRAM or a DRAM, or may be a non-volatile memory such as an NAND, an MRAM or an FRAM. The image storage 11 may also be a storage device such as an optical disc, a hard disk or an SSD. The image storage 11 may be integrated in the inspection assisting apparatus 1, or may be a storage device external to the inspection assisting apparatus 1. The image storage 11 may also be a removable storage medium such as an SD memory card or a USB memory.

The image processor 12 performs image processing on a captured image of the food item. In the case of detecting a feather, the use of a green filter makes the feather clearer than other portions in the captured image. In this image processing, processing to further emphasize the feather is performed. Examples of the image processing include conversion to the HSV color space, conversion to the RGB space, conversion to grayscale and the like, and there is no limitation to a particular method. The image processor 12 saves the processed image in the image storage 11. Note that the saved image may be given an identifier. The identifier may be a number that increments by a constant value, may be a time, or may be determined by other criteria. The image processor 12 may notify the controller 13 of the identifier of the processed image or address information of the region in which the image is stored. It is also possible to perform no image processing on an image captured using the green filter. In that case, the image processor 12 may not be provided.

The controller 13 requests the detection processor 14 to perform processing of detecting foreign matter or a defect on the processed image saved in the image storage 11. The controller 13 may read the processed image from the image storage 11 and provide the read image to the detection processor 14, or the detection processor 14 may directly read the processed image from the image storage 11. In this case, the controller 13 notifies the detection processor 14 of the identifier of the processed image or address information of the region in which the image is stored. In this example, the processed image is provided to the detection processor 14 via the controller 13. However, the image processor 12 may provide the processed image to the detection processor 14 after performing the image processing.

The detection processor 14 performs processing of detecting foreign matter or a defect based on the processed image. In this example, processing of detecting a feather is performed. Note that an image consists of a plurality of pixels and each pixel has a value within a certain range. For example, if one pixel is represented by 8-bit information, the pixel has a value in 256 levels from 0 to 255. The detection processor 14 performs edge detection on the processed image to identify a feather. Specifically, the processed image is first binarized by a threshold. That is, a binary image is generated by converting pixel values greater than or equal to the threshold as 1 and pixel values less than the threshold as 0. The relationship between 1 and 0 may be reversed. As a result of the binarization, all or most portions of the feather become 1, and all or most of other portions become 0. A concentrated region of 1 is detected as a feather region.

Figure 4A:
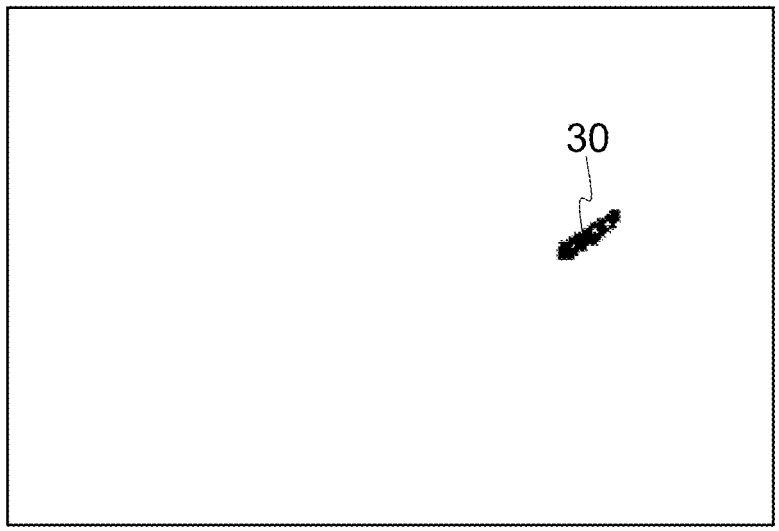
FIGS. 4A and 4B show an example of a binary image and inspection assisting information.

FIG. 4A shows an example of a binary image obtained by binarizing the processed image by a threshold. Black dots correspond to pixels of 1, and other pixels correspond to pixels of 0. There is a short region 30 of pixels with values of 1 on the right side of the image. The region 30 corresponds to the feather region. In the region 30, all pixels may have values of 1, or some pixels may have values of 0. The identification of the region 30 can be performed using clustering, for example. For example, adjacent pixels with values of 1 within a certain distance on the image are classified into the same group, and a group including a certain number of pixels or more is identified as a feather region. While there is one feather region in this example, a plurality of feather regions may be identified. The clustering may use any techniques. Techniques other than clustering may also be used for the region detection.

The assisting information generator 15 generates information representing the position of the feather identified by the detection processor 14. Examples of such information include data indicating the position of the feather. In the present embodiment, frame data enclosing the feather is generated as the data indicating the position of the feather. However, other forms of data may be generated, such as data of an arrow pointing to the feather. The shape of the frame enclosing the feather may be, for example, a rectangle circumscribing the feather, a star enclosing the feather, or other shapes. The frame desirably has a color with a higher contrast than the captured image before being subjected to image processing (the image captured through the green filter). The assisting information generator 15 retains the coordinates of the generated frame data.

The assisting information generator 15 arranges the generated frame data at the retained coordinates on the captured image. The resulting image (assisting image) corresponds to an example of inspection assisting information. A bilayer image may be formed by placing the frame data over the captured image, or the values of pixels corresponding to the position of the frame data may be updated with the values of the frame data. In this manner, an image is obtained in which the feather on the captured image is enclosed by the frame data. Note that, if the size of the binary image is changed from that of the captured image due to scale conversion, scale reconversion may be performed to arrange the frame data on the captured image.

The assisting information generator 15 may arrange information other than frame data on the captured image. For example, since a feather is detected as foreign matter, a text or symbol representing a feather may be arranged near the frame data. For example, text data of "hane (feather)" may be arranged near the frame data. Data representing the size of the detected feather region may also be arranged near the frame data. The size may be at least one of the horizontal or vertical size of the feather region, may be the area (the number of pixels) of the feather region, or may be a size category such as large, medium or small. Data representing the number of identified feather regions may also be arranged. For example, if two feather regions are identified, "2" may be arranged on the captured image. In this case, the number of pieces of frame data is also two. Information other than described above may also be arranged.

Figure 4B:
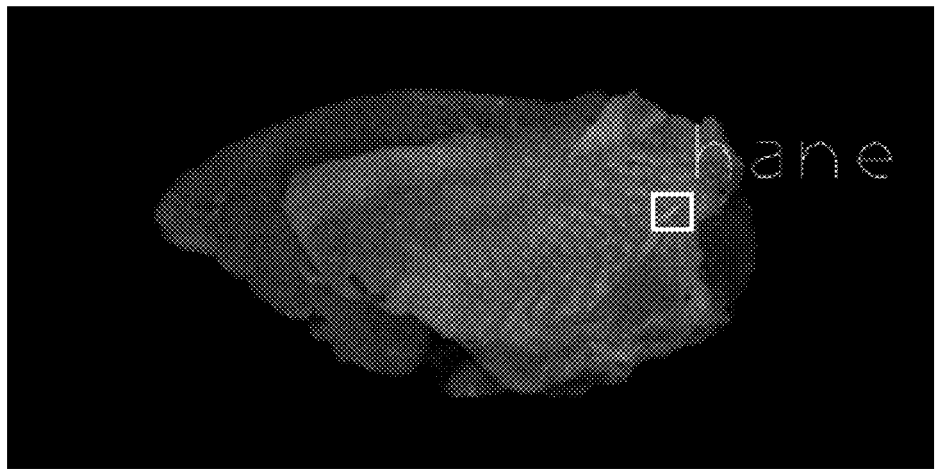

FIG. 4B shows an example of inspection assisting information generated by the assisting information generator 15. Frame data with thick white lines is arranged on the image captured through the green filter, and text data of "hane (feather)" is arranged near the frame data.

The controller 13 receives the inspection assisting information generated by the assisting information generator 15, and stores it in an internal buffer or the image storage 11. The controller 13 controls timing of displaying the inspection assisting information so as to display the inspection assisting information at the timing when the food item to be inspected passes through the inspection area. Specifically, when the controller 13 receives a detection signal from the sensor 24, the controller 13 reads the generated inspection assisting information from the internal buffer or the image storage 11, and sends the read inspection assisting information to the display 3. The display 3 displays the inspection assisting information received from the controller 13. When a predetermined period of time (for example, a period of time obtained by dividing the length of the inspection area by the carrying speed) has elapsed after sending the inspection assisting information, the controller 13 sends, to the display 3, a stop instruction signal to stop the displaying of the inspection assisting information or a standby image. The standby image is an image for being displayed while the worker waits for the entrance of a next target food item into the inspection area. If a plurality of pieces of inspection assisting information are generated by continuously capturing images of the food item, the controller 13 continuously (at constant time intervals) outputs these pieces of inspection assisting information to the display 3. The display 3 continuously displays these pieces of inspection assisting information as a moving image. A sensor may be arranged near the end position of the inspection area such that the sensor sends a detection signal to the controller 13 when detecting the food item, and the controller 13 sends the stop instruction signal or the standby image to the display 3 based on the detection signal.

The controller 13 may use any method to determine which piece of inspection assisting information is to be displayed this time among a plurality of pieces of inspection assisting information sequentially generated for a plurality of food items. For example, the oldest one of the pieces of inspection assisting information that is not displayed yet may be determined as the inspection assisting information to be displayed. In this case, flags may be set to discriminate between inspection assisting information that is already displayed and inspection assisting information that is not displayed yet. Alternatively, inspection assisting information not displayed may be managed by a first-in first-out buffer.

In another method, a sequence number that increments by one for each change of the food item for which the image capturing apparatus 2 performs image capture is given to inspection assisting information generated for the food item. Also, a sequence number that increments by one each time the sensor 24 detects a food item is also generated. Inspection assisting information having a value equal to the sequence number generated for detection by the sensor 24 is determined as inspection assisting information to be displayed this time.

Note that, if food items are carried at long intervals so that a food item is in the inspection area and a next food item to be inspected is not carried to the image-capturing region yet, the inspection assisting information generated most lately may be displayed.

The display 3 receives the inspection assisting information from the controller 13, and displays the received inspection assisting information (refer to FIG. 4B) on the screen 3a. When receiving a stop instruction signal from the controller 13, the display 3 stops displaying the inspection assisting information. When receiving a standby image, the display 3 displays the standby image.

Figure 5A:
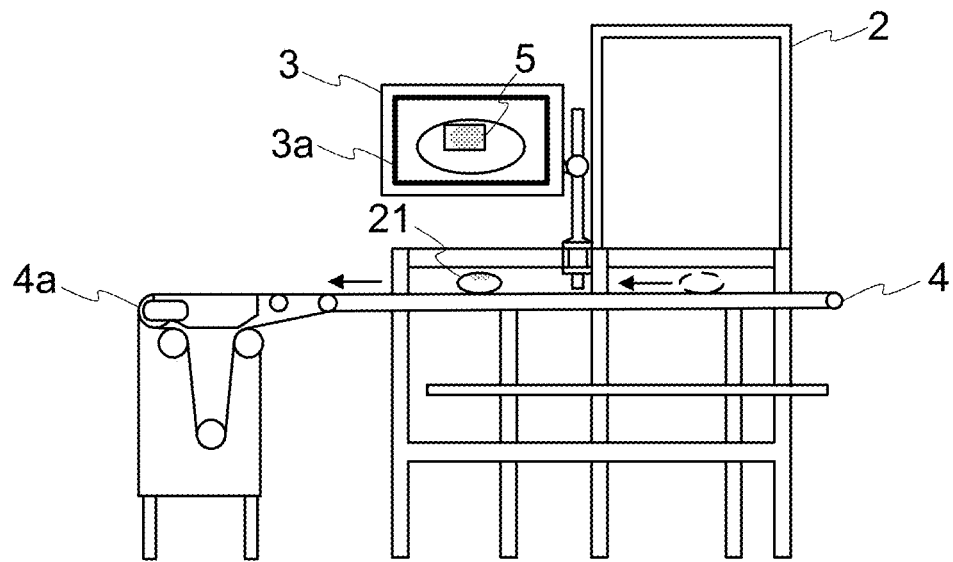
FIGS. 5A and 5B show a specific example of the system according to the first embodiment.
Figure 5B:
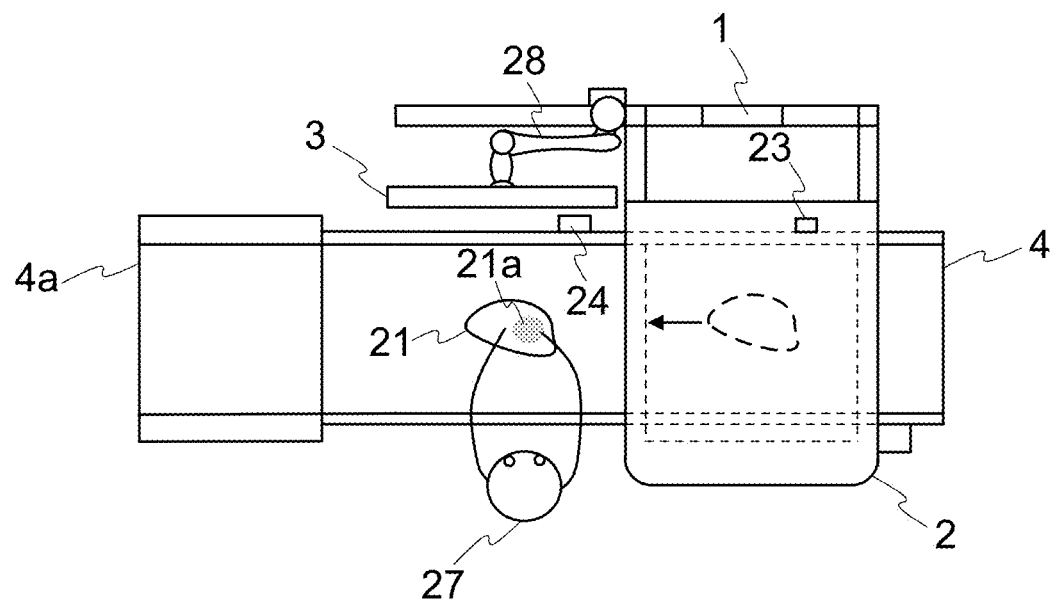

FIG. 5A and FIG. 5B show a specific configuration example of the system. FIG. 5A is a side view of the system. FIG. 5B is a plan view of the system. In FIG. 1 as described above, the left side is the upstream side and the right side is the downstream side as seen toward the paper plane. In FIG. 5A and FIG. 5B, the right side is the upstream side and the left side is the upstream side as seen toward the paper plane. In FIG. 5A, the image capturing apparatus 2, the carrying apparatus 4, the collecting apparatus 4a, the display 3 and a food item 21 are shown. In FIG. 5B, the image capturing apparatus 2, the carrying apparatus 4, the collecting apparatus 4a, the display 3, the food item 21, the sensor 23, the sensor 24, the inspection assisting apparatus 1 and a worker 27 are shown. The following describes a flow of food inspection using the system with reference to FIG. 5A and FIG. 5B.

The food item (chicken) 21 is placed on the conveyor belt of the carrying apparatus 4 on the upstream side, and is carried toward the image capturing apparatus 2. When the food item 21 enters the image-capturing region below the housing of the image capturing apparatus 2, the food item 21 is detected by the sensor 23, and image capture of the food item 21 is performed by a camera in the housing of the image capturing apparatus 2. After the image capture, the food item 21 exits the housing of the image capturing apparatus 2, and is carried toward the downstream side. Meanwhile, the captured image is sent to the inspection assisting apparatus 1, the inspection assisting apparatus 1 detects a feather based on the image, and generates inspection assisting information including information identifying the position of the detected feather (in this example, an assisting image in which rectangular frame data 5 representing the position of the feather is placed over the image of the chicken).

When the food item 21 after exiting the housing of the image capturing apparatus 2 is detected by the sensor 24, the inspection assisting apparatus 1 outputs the generated inspection assisting information described above to the display 3. The display 3 is supported by an arm member 28 such that the screen is vertically oriented to the floor along one side surface of the carrying apparatus 4. The display 3 displays the inspection assisting information input from the inspection assisting apparatus 1 on the screen 3a. Meanwhile, the worker 27 inspects the food item 21 carried to the inspection area by visual check or palpation or by both. Note that, during the inspection, the food item 21 may be held on the carrying apparatus 4, or the food item 21 may be lifted by hand from the carrying apparatus 4. The worker 27 searches the food item 21 for a feather while referring to the inspection assisting information displayed on the display 3 to check the position and size of the frame data 5. The worker removes the feather found. After the feather is removed, the food item is carried by the carrying apparatus 4 toward the downstream side from the inspection area, and is collected by the collecting apparatus 4a.

Figure 6:
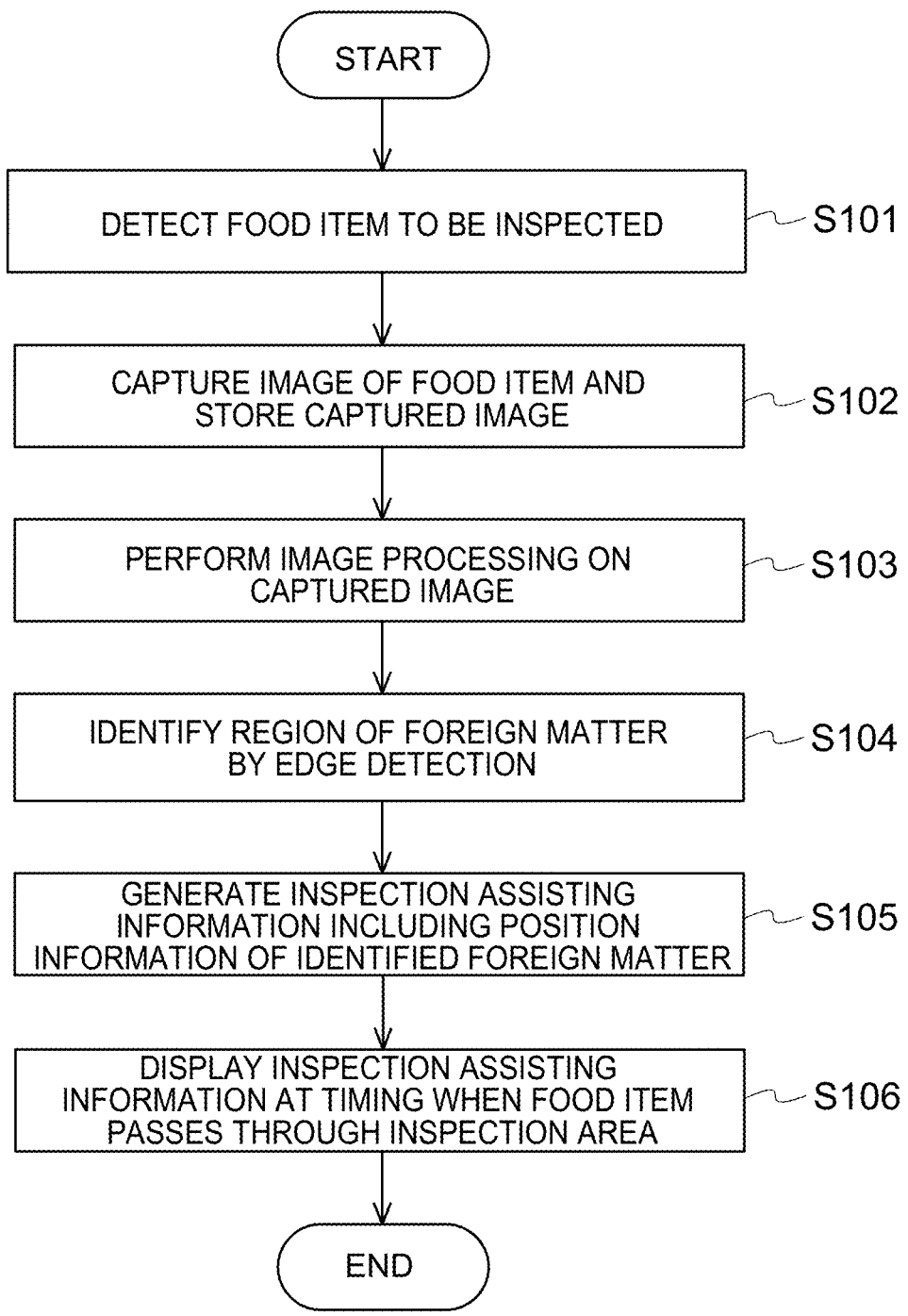
FIG. 6 is a flowchart of an example of operations according to the first embodiment.

FIG. 6 is a flowchart of an example of operations according to an embodiment of the present invention. When the sensor 23 detects that a food item to be inspected enters the image-capturing region of the image capturing apparatus 2 (step S101), the sensor 23 sends a detection signal to the controller 13. The controller 13 outputs a signal for instruction of image capture to the camera 32. The camera 32 captures an image of the food item through a green filter, and the controller 13 stores the captured image in the image storage 11 (S102). The image processor 12 performs image processing on the captured image (S103).

The detection processor 14 performs processing of detecting foreign matter by using edge detection based on the processed image (S104). In this example, processing of detecting a feather as foreign matter is performed. Specifically, the processed image is first binarized by a threshold to generate a binary image. Based on the binary image, a region of pixels of 1 (or 0) is identified as a region of feather.

The assisting information generator 15 generates information representing the identified region of feather (S105). For example, the assisting information generator 15 generates frame data enclosing the feather, and generates an image in which the frame data is arranged on the captured image (inspection assisting information).

The controller 13 receives the generated inspection assisting information, and displays the inspection assisting information on the display 3 at the timing when the food item is carried in the inspection area (S106). If there are a plurality of pieces of inspection assisting information to be displayed, these pieces of inspection assisting information are continuously output to sequentially switch the displaying of these pieces of inspection assisting information. In this manner, the food item and the inspection assisting information displayed on the display 3 appear to move as a moving image in accordance with the movement of the food item on the carrying channel.

While in the present embodiment, the region of foreign matter is identified by performing edge detection on the binary image, other methods may also be used. For example, a model may output information of the position or region of foreign matter by using captured images or processed images as inputs to the model. In this case, the model is constructed by machine learning by using data in which images (captured image or processed images) to be a sample and positions or regions of foreign matter are associated with each other. An example of the model is a neural network.

While in the present embodiment, the sensor 24 detects that the food item is carried to the inspection area, that can be detected by other methods. For example, the timing when the food item appears in the inspection area may be calculated based on the carrying speed of the food item and the distance from the position of capturing the image of the food item (or the position of detection by the sensor 23) to the inspection area. Any method may be used as long as it detects that the food item is carried to the inspection area based on the time required to carry the food item to the inspection area.

According to the present embodiment, accurate and quick inspection of food raw materials can be achieved, and production of high-quality foods and cost reduction can be realized.

(Modified Example 1)

In the first embodiment, a region of feather is identified using a binary image. However, if the food item is a quality item, no feather is contained and a region of feather will not be found. In that case, the assisting information generator 15 generates information indicating that no feather is contained (the food item is a quality item) as inspection assisting information. For example, text data of "NO Hane (Feather)" or "GOOD" is generated. The worker can determine that the food item to be inspected contains no feather by checking the information on the display 3, and the operation of searching for a feather can be omitted.

(Modified Example 2)

As an extension of the modified example 1, the inspection assisting apparatus 1 may determine the food item as a defective item if a feather is detected and determine the food item as a quality item if no feather is detected, and generate information representing whether the food item is a defective item or quality item as inspection assisting information. The worker collects only food items for which information of quality item is displayed in the collecting apparatus 4a, and picks up food items determined as defective items from the carrying apparatus 4 and collects them in a separate container. A sorting apparatus that automatically sorts food items according to whether it is a quality item or defective item may be provided to the carrying apparatus 4 such that the sorting apparatus automatically performs the sorting. In this case, the sorting apparatus receives information of a determination result of whether the food item is a quality item or defective item from the inspection assisting apparatus 1, and performs sorting based on the received information of the determination result.

Second Embodiment

In the second embodiment, blood-containing part is detected from a food item as a defect. The blood-containing part not only refers to a meat portion that is colored due to a bruise or a blood clot, but also includes a colored portion having a different color, taste or the like than other portions. Other examples of defects include those relating to shape such as chipping, cracking, kinks and the like. The system configuration is the same as that in the first embodiment in principle. The following describes differences from the first embodiment.

Figure 7:
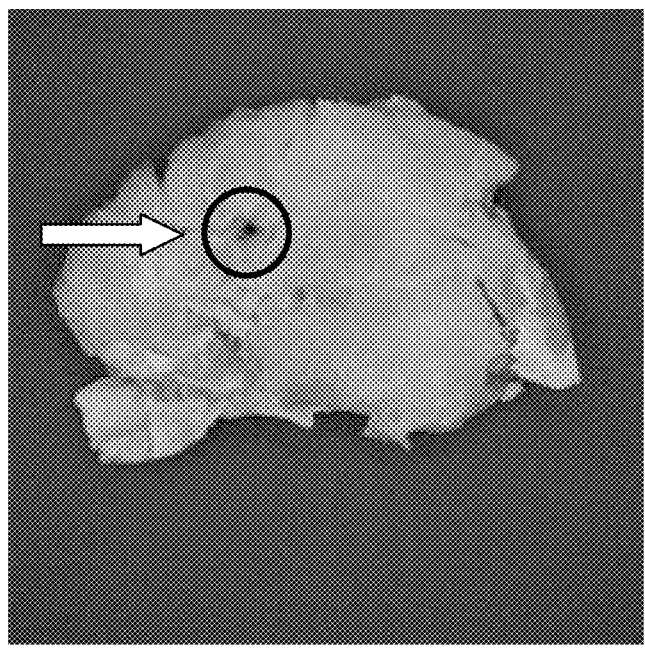
FIG. 7 shows an example of a captured image of chicken according to a second embodiment.

FIG. 7 shows an example of a captured image of chicken according to the present embodiment. The portion enclosed by a circle contains blood-containing part. In the present embodiment, such blood-containing part is detected as a defect of the food item (chicken).

Figure 8:
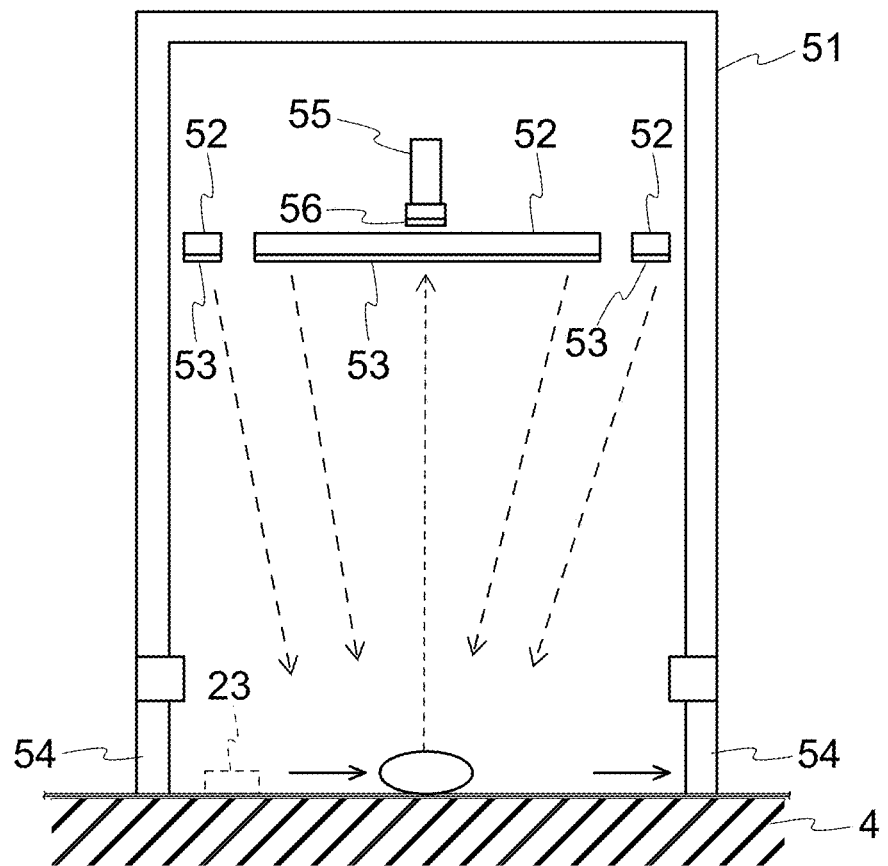
FIG. 8 is a cross-sectional view of an image capturing apparatus according to the second embodiment.

FIG. 8 is a cross-sectional view of an image capturing apparatus 51 according to the present embodiment. In the present embodiment, the image capturing apparatus 51 is used instead of the image capturing apparatus 2 shown in FIG. 1.

The image capturing apparatus 51 includes one or more lighting units 52, a polarizing plate 53, a camera 55, a polarizing plate 56 and a sensor 23. The image capturing apparatus 51 has a housing with a substantially cuboidal shape, and an opening 54 for passing the food item is formed in the bottom part of the housing facing the carrying apparatus 4. The specific structure of the housing is similar to that in the first embodiment, and the description thereof is omitted.

The lighting units 52 are lighting apparatuses using white LEDs, for example. A plurality of lighting units 52 are provided, and the lighting units 52 on the left and right have a shape extending in the direction vertical to the paper plane. The lighting unit 52 at the center includes one or more lighting units with a shape extending in the left and right directions along the paper plane, and the one or more lighting units are arranged at intervals in the direction vertical to the paper plane. Light passing through the intervals is captured by the camera 55 through the polarizing plate 56.

The white LED is an example, and LEDs of different colors may also be used as the light source. For example, a light source may be constructed by combining LEDs of a plurality of colors such as red, green and blue. Other light sources such as an electroluminescence lamp, an HID lamp, a fluorescent lamp and an incandescent lamp may also be used. The type of the light source used can be determined according to the type of the food item or foreign matter to be detected. The light source is not limited to a light source that emits visible light, and may be a light source that emits infrared light, ultraviolet light or the like, or may be a combined light source of a plurality of wavelengths (multi-wavelength).

The polarizing plate 53 is provided on the front side of the lighting unit 52. For example, the polarizing plate 53 is a linear polarizing plate. Providing the polarizing plate 53 reduces diffuse reflection of light from the surface of the carrying apparatus 4 or water or oils and fats in the food item, and contributes to accurate image capture of the food item by the camera 55. Configurations without the polarizing plate 53 are also possible.

The camera 55 captures an image of the food item irradiated with beams of light from the lighting unit 52. The polarizing plate 56 is provided on the front side of the camera 55. For example, the polarizing plate 56 is a polarizing filter for camera lenses. By performing image capture through the polarizing plate 53, an image can be obtained with reduced effects of diffuse reflection or sheens due to the luster of water, oils and fats and the like. Configurations without the polarizing plate 56 are also possible.

The image processor 12 extracts the luminance of each color of red, green and blue (RGB) for the pixels in a captured image, which is output information of the image capturing apparatus 51, and obtains an image for each color. The image processor 12 then generates an image by subtracting the pixel values of the green (G) image from the red (R) image for each pixel. The image thus generated is subjected to binarization processing using a threshold to generate a binary image, in a manner similar to that in the first embodiment.

Figure 9:
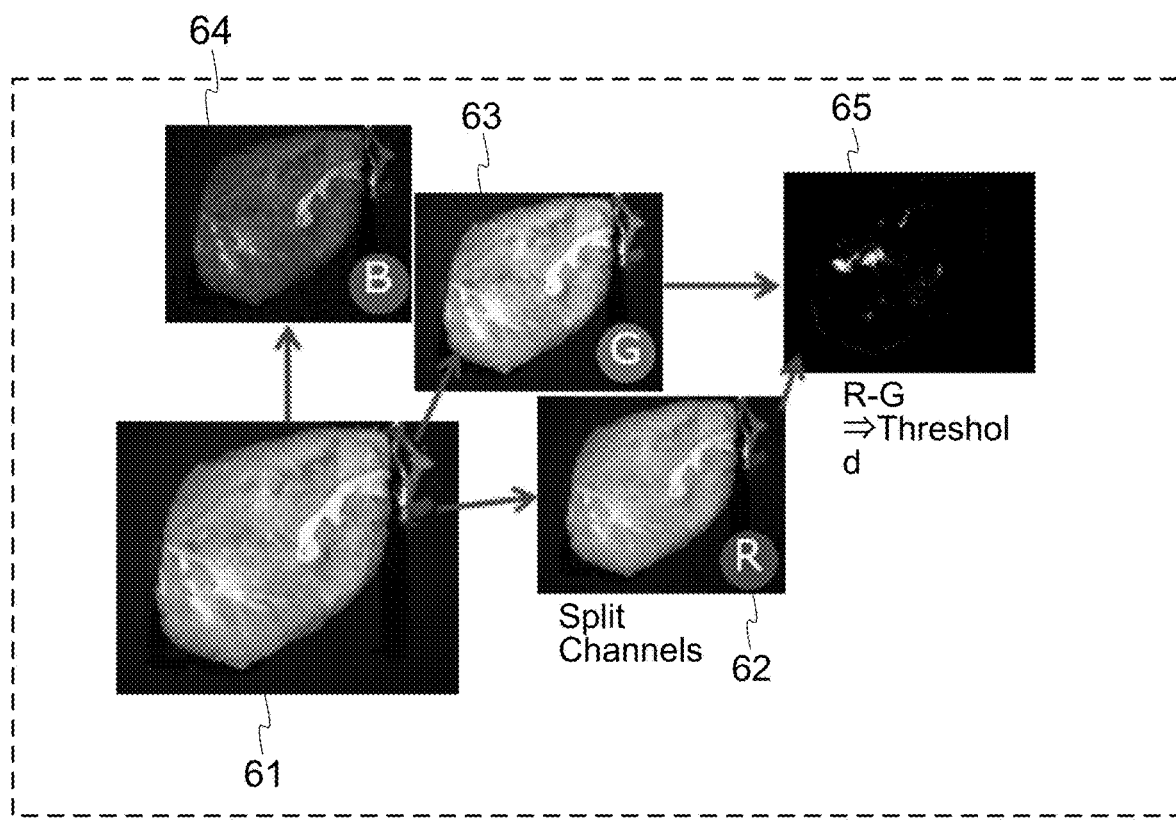
FIG. 9 shows a specific example of image processing according to the second embodiment.

FIG. 9 shows a specific example of image processing. A captured image 61 is separated into an R image 62, a G image 63 and a B image 64. The pixel values of the G image 63 are subtracted from the pixel values of the R image 62 to generate an image (R-G image). The generated image is subjected to binarization processing to generate a binary image 65. The captured image 61 is a color image, and the images 62 to 64 are grayscale images expressing the magnitudes of luminance for respective colors of R, G and B. In the binary image 65, pixels with values greater than or equal to the threshold are white, and pixels with values less than the threshold are black. A region of pixels with values greater than or equal to the threshold corresponds to a portion of blood-containing part.

The detection processor 14 can identify the region of blood-containing part (a white region in the binary image 65) by performing edge detection on the binary image 65 in a manner similar to that in the first embodiment.

Note that the image processing described above is an example, and other types of image processing may be performed. For example, after performing processing to emphasize the red and green colors on a captured image, the captured image on which the processing has been performed may be separated into an R image, a G image and a B image. Besides, after performing conversion (for example, conversion to the HSV color space) of an image obtained by subtraction (R-G image), an image may be generated by extracting the red components from the converted image. An image may also be generated by extracting the red components from the R-G image without converting the R-G image. Note that it is also not prohibited to perform binarization processing on a captured image without performing any image processing on the captured image.

The assisting information generator 15 generates inspection assisting information including information identifying the position of blood-containing part, in a manner similar to that in the first embodiment. For example, the assisting information generator 15 generates frame data enclosing the region of blood-containing part based on the binary image, and arranges the generated frame data on the captured image. Text data such as "blood-containing part" may be arranged near the frame data. The image thus generated (assisting image) is displayed on the display 3 as inspection assisting information. The control of display timing is similar to that in the first embodiment. The worker inspects the food item carried into the inspection area while referring to the frame data as inspection assisting information displayed on the display 3 to check the position of the blood-containing part. When finding the blood-containing part, the worker removes the blood-containing part using a predetermined tool. Alternatively, the worker may check the blood-containing part so that, if the blood-containing part is of an allowable extent (e.g., small), the worker allows the food item to be collected by the collecting apparatus 4a, and if the blood-containing part is not of an allowable extent, the worker stores it in a predetermined case for separately performing the operation of removing the blood-containing part in another step. Other methods may be used to deal with chicken for which blood-containing part is detected.

(Modified Example)

In the second embodiment described above, an R-G image is generated and a binary image is generated from the R-G image as image processing (refer to FIG. 9). In this modified example, an infrared (INFRARED) image is captured in addition to a color image, and the pixel values of the G image are subtracted from the pixel values of the infrared image to generate an image. A specific example of the infrared image is a near-infrared (NEAR INFRARED) image. Near-infrared light is electromagnetic waves with wavelengths between 760 nm and 1000 nm, for example. In this modified example, a near-infrared image is captured, and the pixel values of the G image are subtracted from the pixel values of the near-infrared image to generate an image (NIR-G image). Further, the NIR-G image is subjected to binarization processing to generate a binary image. This binary image is used to detect foreign matter or a defect. In this manner, the accuracy of detecting darker blood-containing part (for example, highly blackish blood-containing part) can be improved.

In this modified example, a camera capable of capturing both color images and near-infrared images is used as the camera 55. As an example of such a camera, the combination of both an RGB camera and an infrared camera may be used. Alternatively, a multispectral camera or a hyperspectral camera capable of capturing images of a larger number of wavelengths may be used. The configuration, number and type of the camera are not particularly limited. If both of an RGB camera and an infrared camera are used, image capture may be performed at the same time or in an order. In the latter case, the image processor 12 at a later step may perform alignment of the images for performing the subtraction processing on the images.

The color image and near-infrared image of the food item (chicken) captured by the camera 55 are sent to the image storage 11. The image storage 11 stores the color image and near-infrared image therein. The image processor 12 reads the color image from the image storage 11, and extracts the luminance of each color of red, green and blue (RGB) from the color image, to generate an R image (red image) 131, a G image (green image) 132 and a B image (blue image) 133.

Figure 10:
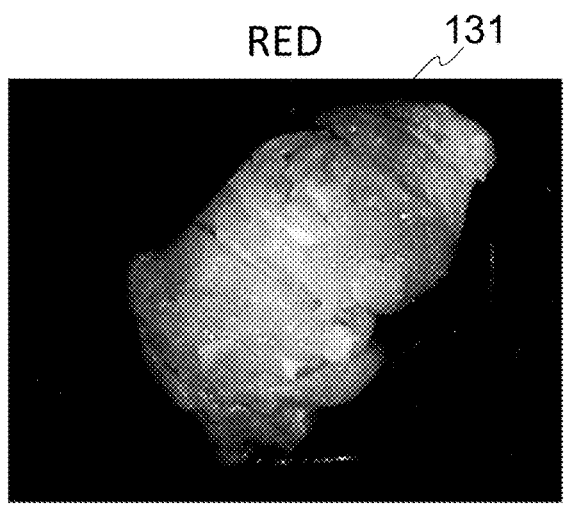
FIG. 10 shows an example of an image captured by a camera according to a modified example of the second embodiment.
Figure 10:
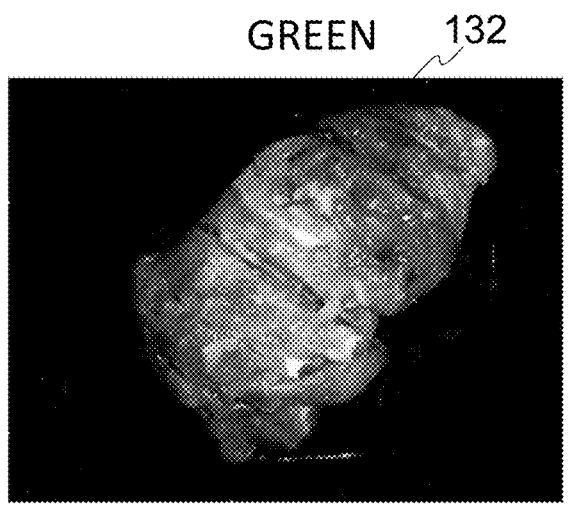
Figure 10:
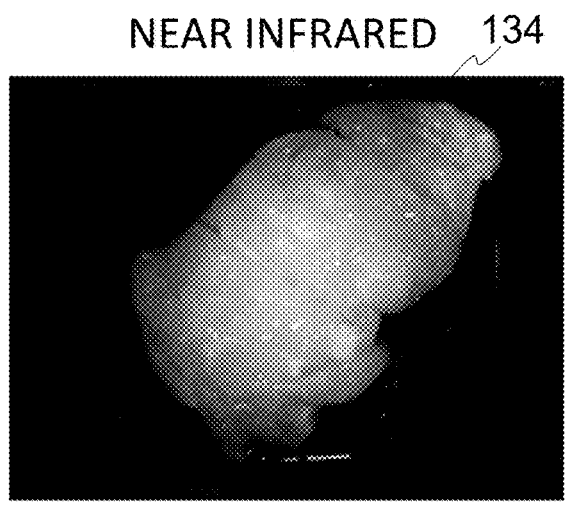
Figure 10:
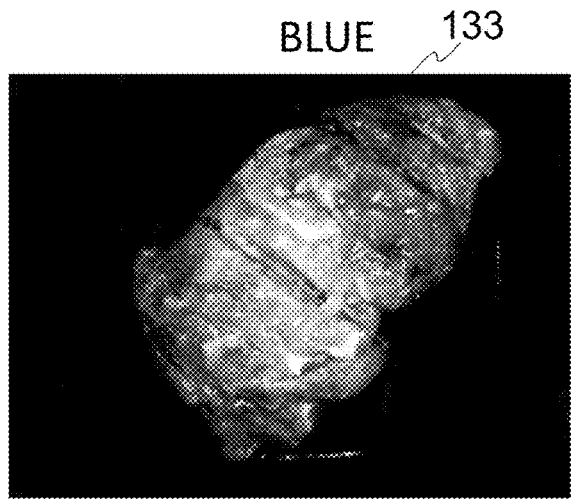

FIG. 10 shows an example of the R image 131, G image 132 and B image 133 generated by the image processor 12. The figure also shows an example of a near-infrared image 134 stored in the image storage 11. In the images 131 to 134, the intensity of electromagnetic waves of respective wavelengths is represented by a grayscale tone (luminance) for each pixel. A pixel with a higher intensity is shown to be brighter. A pixel with a smaller intensity is shown to be darker. In any of the images 131 to 134, the portion of meat stands out with brighter colors than the surrounding portions. This example uses a sample containing only highly blackish blood-containing part.

The image processor 12 generates an image (NIR-G image) by subtracting the pixel values of the G image 132 from the near-infrared image 134 for each pixel, that is, generates a difference image between the near-infrared image 134 and the G image 132. The image processor 12 performs binarization processing on the NIR-G image to generate a binary image (NIR-G binary image) 135. The detail of the binarization processing is described above.

Figure 11:
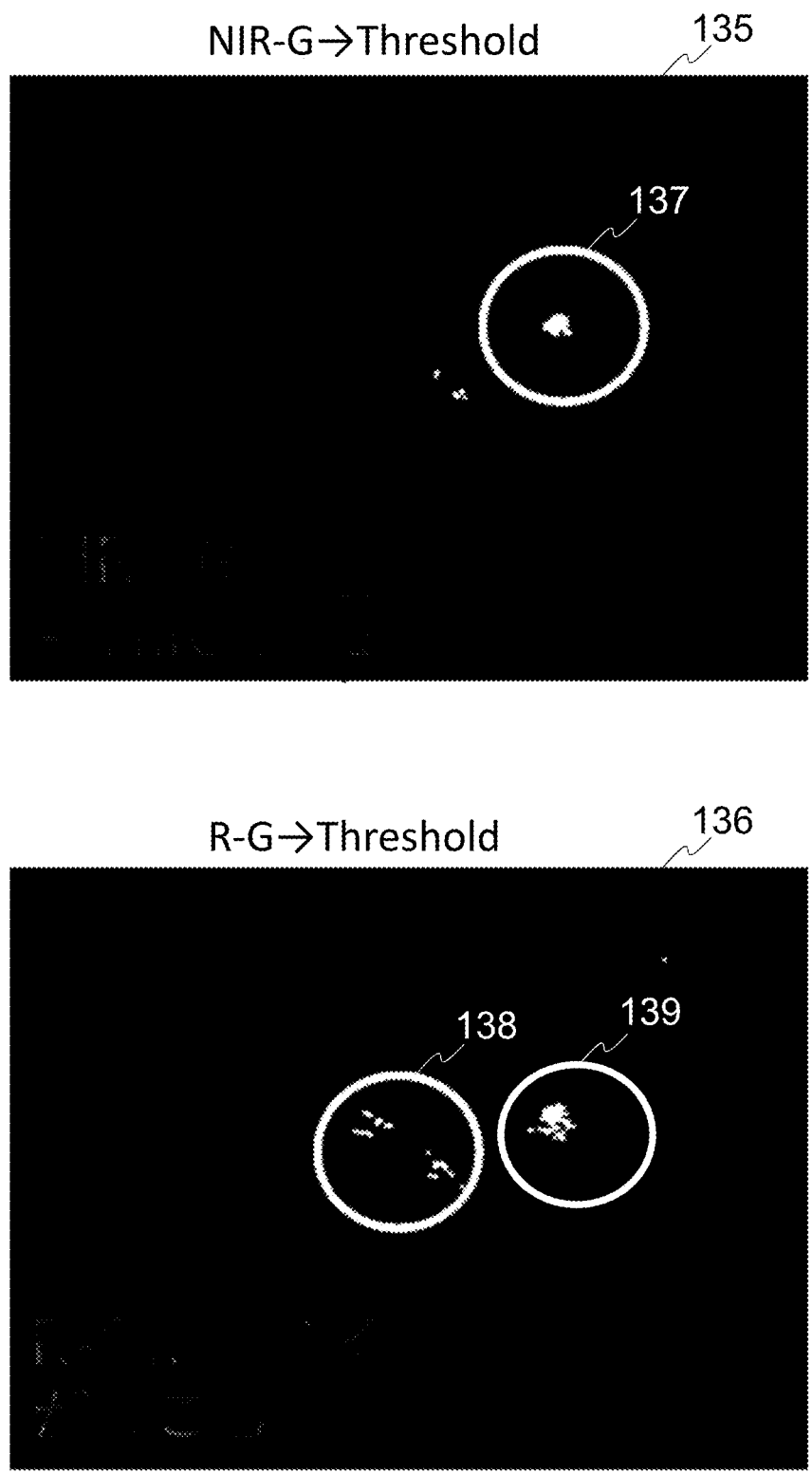
FIG. 11 shows an example of respective binary images according to the second embodiment and the modified example thereof.

The upper side of FIG. 11 shows an example of the NIR-G binary image 135 generated by the image processor 12. The lower side of FIG. 11 shows an example of a binary image (R-G binary image) 136 obtained by performing binarization processing on an image (R-G image) obtained by subtracting the pixel values of the G image 132 from the R image 131 for each pixel. The R-G image corresponds to the difference image between the R image 131 and the G image 132. The R-G binary image 136 is shown for comparison with the NIR-G binary image 135, and it is not necessarily required to generate the R-G binary image 136 in this modified example.

In the NIR-G binary image 135 and R-G binary image 136, pixels with values greater than or equal to the threshold are white, and pixels with values less than the threshold are black. A region of pixels with values greater than or equal to the threshold corresponds to the blood-containing part.

Referring to the R-G binary image 136 on the lower side of the FIG. 11, while the pixels of the portion of highly blackish blood-containing part are detected in a region 139 enclosed by a circle, a lot of noise components appear at portions where actually no blood-containing part is contained, as shown in a region 138 enclosed by a circle. This is because a low threshold is used for generating the R-G binary image 136 in order to detect highly blackish blood-containing part.

On the other hand, in the NIR-G binary image 135 on the upper side of FIG. 11, while the pixels of the portion of highly blackish blood-containing part are detected in a region 137 enclosed by a circle, only a little amount of noise components appear in the region corresponding to the region 138 of the R-G binary image 136. This is because the NIR-G image can emphasize the portion of blackish blood-containing part, and it is not necessary to lower the threshold for generating the NIR-G binary image 135 as much as for the R-G binary image 136. That is, a higher threshold is used for the NIR-G binary image 135 than for the R-G binary image 136. Thus, the use of the NIR-G binary image 135 enables both of reduction of noise components and enhancement of the accuracy of detecting highly blackish blood-containing part.

In this modified example, other types of images may be used instead of a near-infrared image. For example, images of other types of infrared light than near-infrared light (such as far-infrared light), ultraviolet images or three-dimensional images may also be used. Images of the other types of infrared light can be captured by using, for example, a camera provided with a sensor with sensitivity to the other types of infrared light. Ultraviolet images can be captured by using, for example, a camera provided with a sensor with sensitivity to the ultraviolet light. Three-dimensional images can be captured by using, for example, a 3D camera.

Also, while operation (subtraction) is performed between the near-infrared image and the G image in this modified example, the combination of images to be operated is not limited to the combination of the near-infrared image and the G image. That is, combinations of any types of images can be subjected to the operation as long as the foreign matter or defect to be detected can be accurately detected. For example, two or more of a near-infrared image, an image of other types of infrared light, an ultraviolet image, a three-dimensional image, an R image, a G image and a B image can be subjected to the operation. The type of the operation is not limited to subtraction, and may also be addition, subtraction, multiplication, division or combinations thereof. The images may also be multiplied by weighting coefficients before performing the operation.

The modified examples of the first embodiment are similarly applicable to the present embodiment.

Third Embodiment

While the first and second embodiments use the display 3 as an information output apparatus that outputs inspection assisting information, the third embodiment uses a projector, which is an example of a projection apparatus, to project the inspection assisting information onto the food item being carried or onto the carrying channel. The following describes the present embodiment in details.

Figure 12:
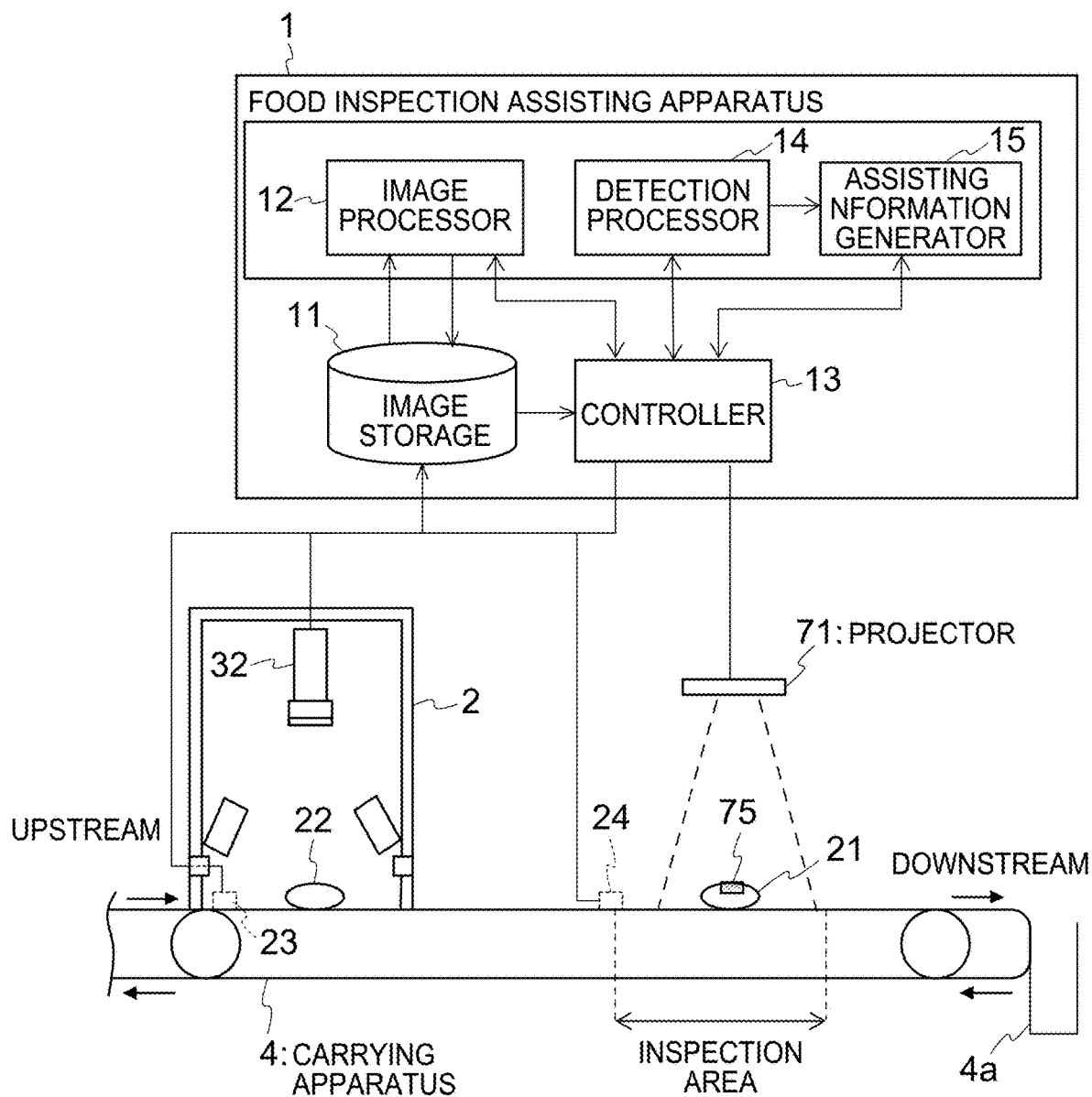
FIG. 12 shows an example of a food inspection assisting system according to a third embodiment.

FIG. 12 shows an example of a food inspection assisting system according to the third embodiment. A projector 71 is used in place of the display 3 in FIG. 1. The projector 71 is provided above the carrying channel in the inspection area, and projects inspection assisting information toward the carrying surface. Other configurations are similar to those in the first embodiment in principle. The following mainly describes changes or extensions from the first embodiment.

Figure 13A:
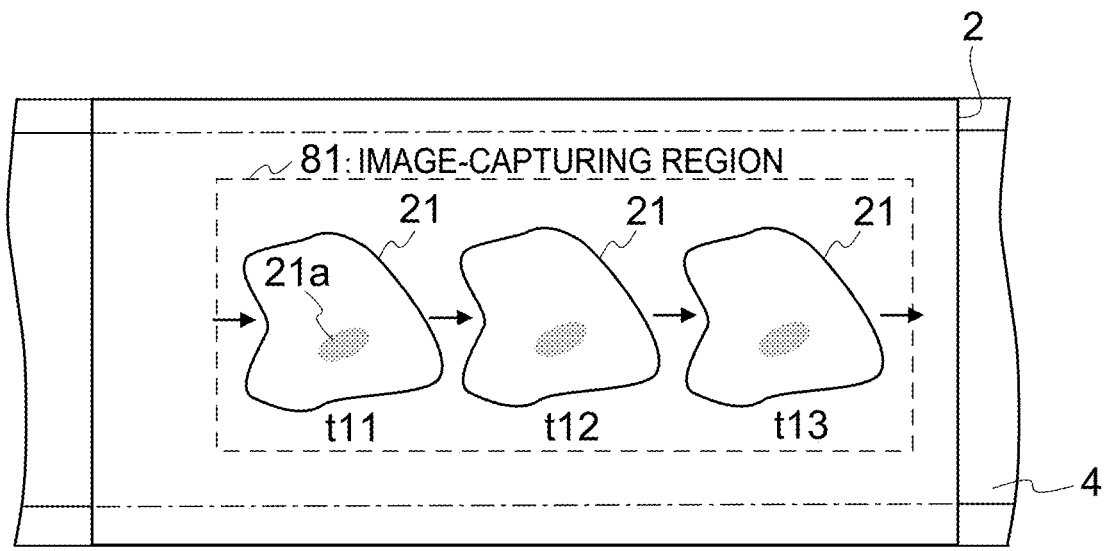
FIGS. 13A and 13B illustrate continuous image capture performed by the image capturing apparatus and continuous projection performed by a projector.

FIG. 13A illustrates an example of continuous image capture performed by the image capturing apparatus 2. When chicken (food item) 21 carried by the carrying apparatus 4 enters an image-capturing region 81 in the image capturing apparatus 2, a plurality of times of image capture (continuous shooting of static images) is performed at constant time intervals. The figure shows an example in which image capture is performed three times in total at time t11, time t12 and time t13. Since the food item moves even during the plurality of times of image capture, the position of the food item in the captured images gradually changes in the carrying direction. While three times of image capture is performed in this example, the number of times or rate of performing image capture may be determined as required.

Figure 14A:
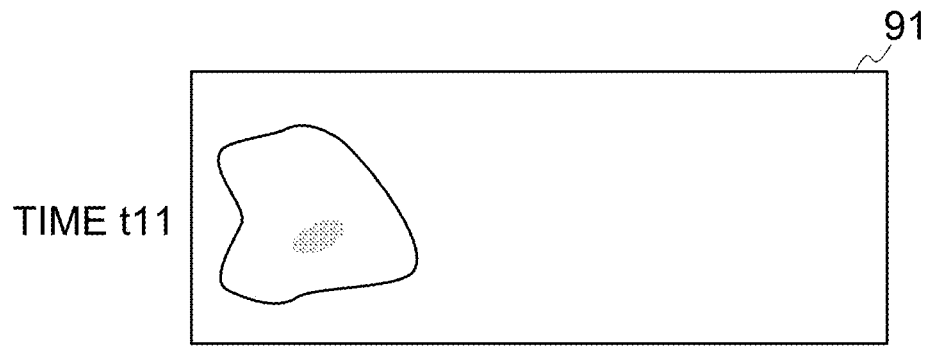
FIGS. 14A to 14C show an example of captured images obtained by continuous image capture.
Figure 14B:
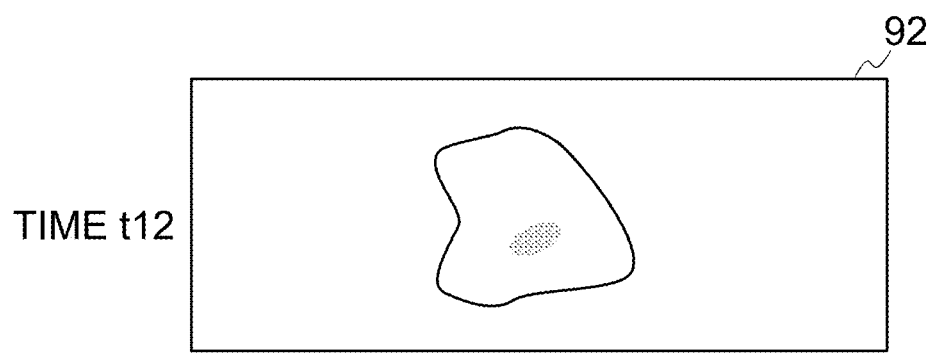
Figure 14C:
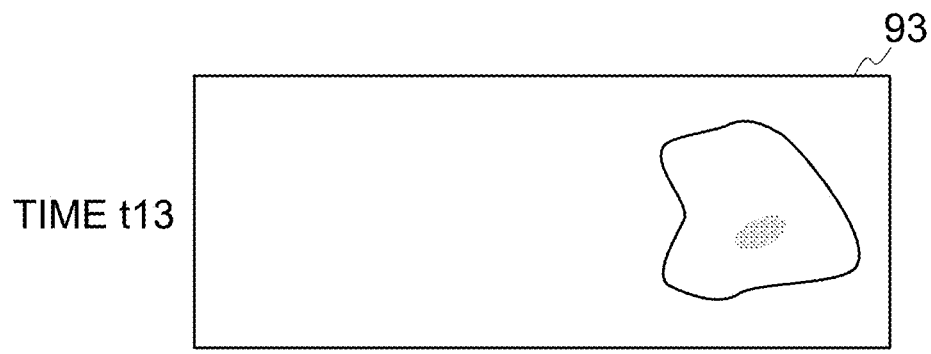

FIG. 14 shows an example of captured images obtained by continuous image capture. FIG. 14A shows an image 91 captured for a first time at time t11, FIG. 14B shows an image 92 captured for a second time at time t12, and FIG. 14C shows an image 93 captured for a third time at time t13. In the captured images 91 to 93, the food item that is the subject of image capture gradually moves in the carrying direction.

The image capturing apparatus 2 sends, to the inspection assisting apparatus 1, the plurality of captured images obtained by the continuous image capture. The inspection assisting apparatus 1 generates a plurality of pieces of inspection assisting information for the plurality of captured images in a manner similar to that in the first embodiment. In this example, each piece of inspection assisting information is obtained by arranging frame data on each captured image, in a manner similar to that in the first embodiment.

When the controller 13 receives a detection signal for the food item from the sensor 24, the controller 13 controls the projector 71 such that the plurality of pieces of inspection assisting information are continuously (for example, at constant time intervals) projected. The controller 13 outputs the plurality of pieces of inspection assisting information to the projector 71 at constant time intervals. The projector 71 sequentially projects the plurality of pieces of inspection assisting information input from the controller 13 onto the carrying channel at constant time intervals. For example, the size of the irradiation region of the projector 71 is the same as that of the image-capturing region of the image capturing apparatus 2.

Figure 13B:
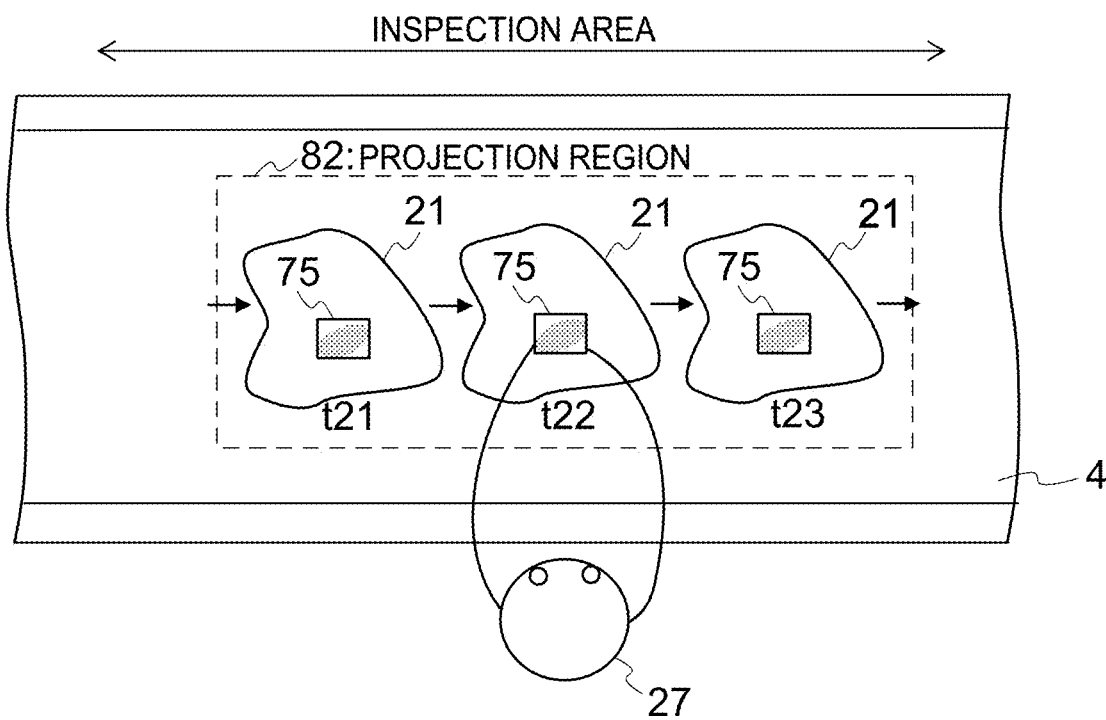
Figure 15A:
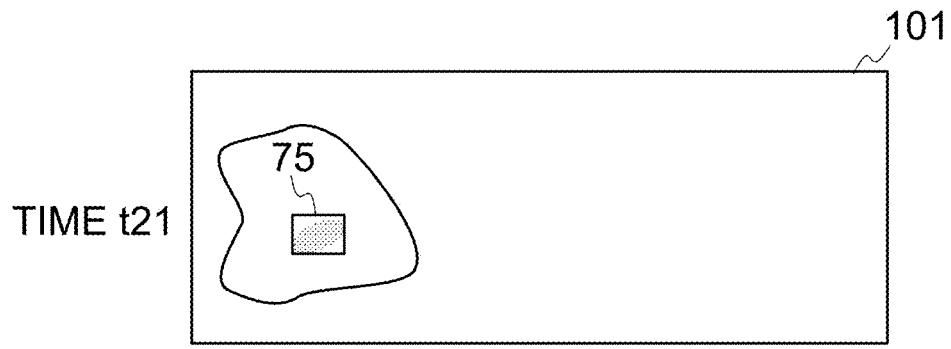
FIGS. 15A to 15C show an example of a plurality of pieces of inspection assisting information continuously projected.
Figure 15B:
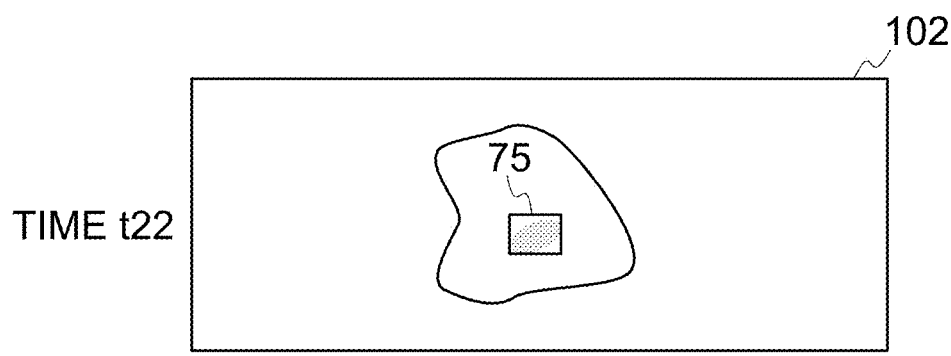
Figure 15C:
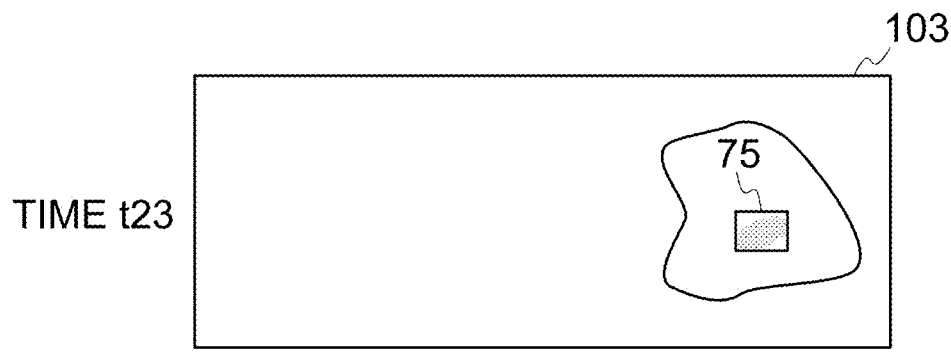

FIG. 13B shows an example of projection performed by the projector 71. After exiting the housing of the image capturing apparatus 2, the chicken (food item) 21 is carried by the carrying apparatus 4 and enters a projection region 82 of the projector 71. At this time, the plurality of pieces of inspection assisting information are projected by the projector 71 at constant time intervals. FIG. 15 shows an example of a plurality of pieces of inspection assisting information continuously projected. FIG. 15A shows inspection assisting information 101 projected for a first time at time t21, FIG. 15B shows inspection assisting information 102 projected for a second time at time t22, and FIG. 15C shows inspection assisting information 103 projected for a third time at time t23. The respective pieces of information correspond to the captured images of FIG. 14A to FIG. 14C. In the inspection assisting information 101 to 103, the food item gradually moves in the carrying direction, and frame data 75 moves correspondingly in the carrying direction by the same amounts. The pieces of inspection assisting information of FIG. 15A to FIG. 15B are sequentially projected, so that the inspection assisting information (food item images and frame data) is projected over the food item being carried, as shown in FIG. 13B. The food item moves even during the image capture by the projector 71, and the food item and frame included in the inspection assisting information projected at time t21, time t22 and time t23 also move at the same speed. Thus, the images of the food item and frame included in the inspection assisting information are projected as conforming to the position of the food item regardless of the movement of the food item. Therefore, the frame projected on the carried food item contains foreign matter (feather). The worker can see that the feather is contained in the frame projected on the food item, and can easily find the feather.

Figure 16:
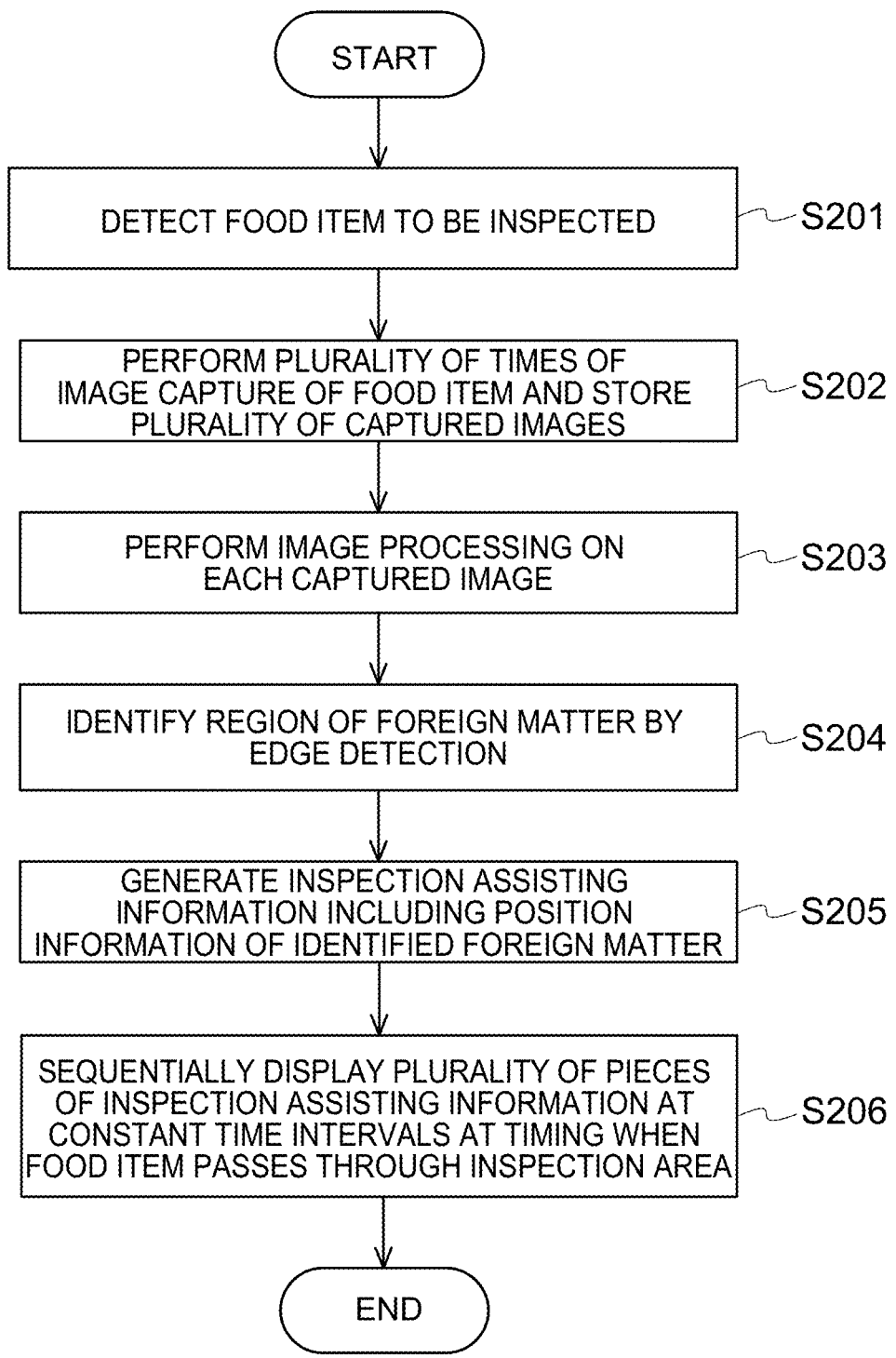
FIG. 16 is a flowchart of an example of operations according to the third embodiment.

FIG. 16 is a flowchart of an example of operations according to an embodiment of the present invention. When the sensor 23 detects that a food item to be inspected enters the image-capturing region of the image capturing apparatus 2 (step S201), the sensor 23 sends a detection signal to the controller 13. The controller 13 outputs a signal for instruction of image capture to the camera 32. The camera 32 performs a plurality of times of image capture (continuous image capture) of the food item at constant time intervals through a green filter, and the controller 13 stores the plurality of captured images in the image storage 11 (S202). The image processor 12 performs image processing on each captured image. Specifically, the image processor 12 generates an image by performing image processing on each captured image (S203).

The detection processor 14 performs processing of detecting foreign matter by using edge detection based on the processed image (S204). In this example, processing of detecting a feather as foreign matter is performed. Specifically, the detection processor 14 first binarizes the processed image by a threshold to generate a binary image. Based on the binary image, a region of pixels of 1 (or 0) is identified as a feather region.

The assisting information generator 15 generates information representing the position of the identified feather region (S205). For example, the assisting information generator 15 generates frame data enclosing the feather, and generates an image in which the frame data is arranged on the captured image (inspection assisting information).

The controller 13 receives the plurality of pieces of inspection assisting information generated for the plurality of captured images, and sequentially outputs the plurality of pieces of inspection assisting information to the projector 71 at constant time intervals at the timing when the food item to be inspected passes through the inspection area. In this manner, the plurality of pieces of inspection assisting information are projected onto the food item being carried on the carrying channel at constant time intervals (S206). This allows the position of the frame data included in the projected inspection assisting information to be moved in accordance with the movement of the food item on the carrying channel, so that the worker can continue checking the frame projected on the foreign matter (feather) in the food item without interruption. Thus, the worker can easily identify and remove the feather.

While in the present embodiment, the image-capturing region (image-capturing direction) of the camera 32 and the projection region (projection direction) of the projector 71 are fixed, in the case of performing continuous image capture of the food item, the direction of the camera 32 may be moved while capturing images of the food item. Similarly, the projection direction of the projector 71 may be moved while sequentially projecting the plurality of pieces of inspection assisting information. This allows the use of a camera with a narrow angle of view and a projector with a narrow angle of projection.

In the present embodiment, images in which frame data is arranged on captured images are projected onto the food item as inspection assisting information. However, images including only frame data (not including chicken) may be generated as inspection assisting information and projected onto the food item.

While in the present embodiment, the inspection assisting information is projected onto the food item, the inspection assisting information may also be projected onto the carrying channel. For example, the inspection assisting information may be projected onto a part of the carrying channel near (for example, on the right of, on the left of, above or below) the food item being carried. In this case as well, the position of the projected information changes in synchronization with the food item being carried. In this manner, the worker can perform inspection while looking at the inspection assisting information displayed near the food item being carried.

While in the present embodiment, a projector that projects information by light is used as an information output apparatus, a beam projector that projects information by light beams may also be used. In the case of using a beam projector, light beams may be projected onto the position of detected foreign matter. The projected beams may also be moved to enclose the foreign matter. In any case, the position of the projected beams changes in synchronization with the food item being carried. Such projection of light beams is also a form of displaying inspection assisting information.

While the present embodiment has been described by using an example of detecting foreign matter (feather) based on the first embodiment, the same may apply to embodiments of detecting a defect (such as blood-containing part) such as the second embodiment.

Fourth Embodiment

In the first to third embodiments, processing of detecting foreign matter or a defect in a food item is performed based on captured images, and inspection assisting information obtained according to the result of detection is generated and displayed. In the present embodiment, characteristic information of a food item is measured, and inspection assisting information obtained according to the measured characteristic information is generated and displayed. Other points are similar to those in the above-described embodiments in principle.

Figure 17:
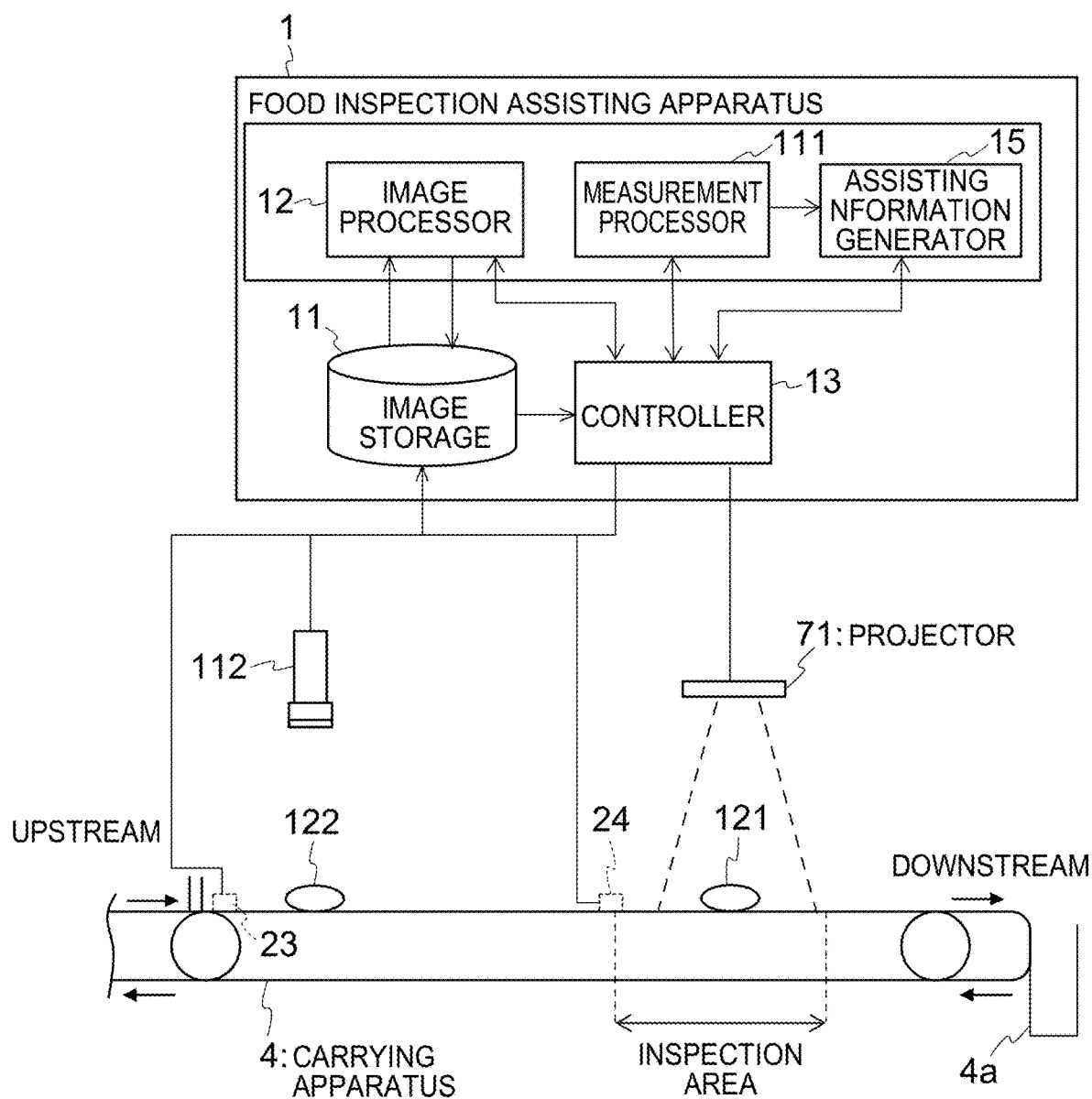
FIG. 17 shows an example of a food inspection assisting system according to a fourth embodiment.

FIG. 17 shows an example of a food inspection assisting system according to the present embodiment. The image capturing apparatus 2 in FIG. 12 used in the third embodiment is replaced with a three-dimensional camera (3D camera) 112, and the detection processor 14 is replaced with a measurement processor 111. Elements with the same names as in FIG. 12 are provided with the same reference numerals. The following mainly describes changes and extensions from the third embodiment.

The 3D camera 112 captures an image of a food item to be inspected. The 3D camera 112 is an example of a sensing apparatus. The 3D camera 112 measures the color and depth of the food item, and acquires a 3D image, which is output information of the 3D camera 112, as a captured image. The 3D image includes the color information and depth for each pixel. The depth can be measured using an LED that emits infrared light and a sensor that receives reflected infrared light, for example. When the sensor 23 detects the food item 122, the sensor 23 outputs a detection signal to the controller 13. The controller 13 receives the detection signal and outputs a signal for instruction of image capture to the 3D camera 112, and the 3D camera 112 performs image capture. The number of times of image capture is one or more. The following description assumes the case of performing a plurality of times of image capture (continuous image capture).

The image processor 12 performs preprocessing on the 3D image. For example, the image processor 12 performs processing of reducing noise components (averaging), contrast adjustment, tone adjustment and the like. Configurations without performing any preprocessing are also possible.

The measurement processor 111 measures characteristic information of the food item based on the 3D image. For example, the measurement processor 111 measures the weight of the food item. The weight is calculated by measuring the volume of the food item based on the 3D image and multiplying the volume by an averaged density of the food item (chicken). The averaged density of the chicken is provided to the measurement processor 111 in advance, or is stored in a storage unit such as a memory accessible to the measurement processor 111. Besides the weight, the size (at least one of the length, width and height) of the chicken may also be measured. The fat proportion of the chicken may also be calculated. For example, all portions of pixels with luminance values greater than or equal to a predetermined value (whitish parts of the chicken) in the depth direction are regarded as fat portions, and the fat proportion is calculated from the proportion of the entire volume of the chicken and the volume of the fat portions. Note that, while the present embodiment uses a 3D camera to measure the characteristic information of the food item, visible light or ultraviolet light can also be used to perform the measurement. Also, instead of the 3D camera, a weight sensor, which is a sensing apparatus, may be arranged in the carrying apparatus 4 so that the weight sensor detects the weight of the chicken.

The assisting information generator 15 generates inspection assisting information based on the characteristic information of the food item measured by the measurement processor 111. Specifically, the assisting information generator 15 generates an image in which the characteristic information of the food item is arranged at the position of (placed over) the chicken in a three-dimensional image or a two-dimensional image obtained by removing depth information. Alternatively, an image in which the characteristic information is arranged at the same position as the chicken and no image of chicken is contained may be generated.

The controller 13 receives a plurality of pieces of inspection assisting information generated for a plurality of captured images (3D images). When the controller 13 receives a detection signal for the food item 121 from the sensor 24, the controller 13 controls the projector 71 such that the plurality of pieces of inspection assisting information are projected at constant time intervals. The controller 13 outputs the plurality of pieces of inspection assisting information to the projector 71 at constant time intervals. The projector 71 sequentially projects the plurality of pieces of inspection assisting information input from the controller 13 onto the carrying channel at constant time intervals. For example, the size of the irradiation region of the projector 71 is the same as that of the image-capturing region of the image capturing apparatus 2.

Figure 18:
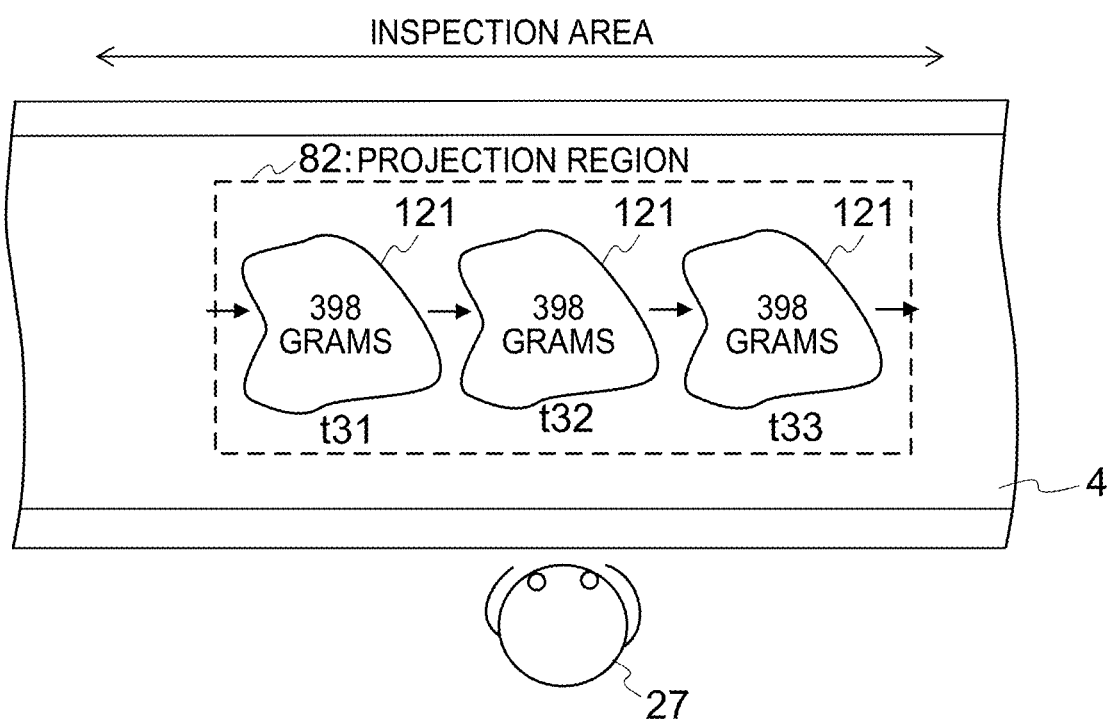
FIG. 18 shows projection performed by a projector.

FIG. 18 shows an example of projection performed by the projector 71. The chicken (food item) 121 is carried by the carrying apparatus 4 and enters a projection region 82 of the projector 71. At this time, the plurality of pieces of inspection assisting information are projected by the projector 71 at constant time intervals. Similar to the third embodiment, the inspection assisting information (including the characteristic information of the food item) is projected over the food item being carried. In the example of the figure, text data of "398 grams" is projected onto the chicken 121 to be inspected. The food item 121 moves even during the image capture by the projector 71, and the characteristic information included in the inspection assisting information projected at time t31, time t32 and time t33 moves accordingly. The characteristic information is projected over the food item regardless of the movement of the food item. The worker determines if the weight of the chicken is in a range defined by the specifications by checking the value of the weight projected on the food item. If the weight is in the range defined by the specifications, the chicken is regarded to be qualified and is allowed to be collected by the collecting apparatus 4a. If the weight is out of the specification range, the chicken is picked up from the carrying channel by hand, and is contained in a case separately prepared. In the example of the figure, the weight is in the specification range, and the worker determines that there is no problem and lets the chicken 121 go. The pieces of chicken collected in the case are subjected to weight adjustment in a later operation to fall within the specification range. Alternatively, and conversely, pieces of chicken that fall within the specification range may be picked up and contained in a case separately prepared, and pieces of chicken out of the specification range may be collected by the collecting apparatus 4a.

Figure 19:
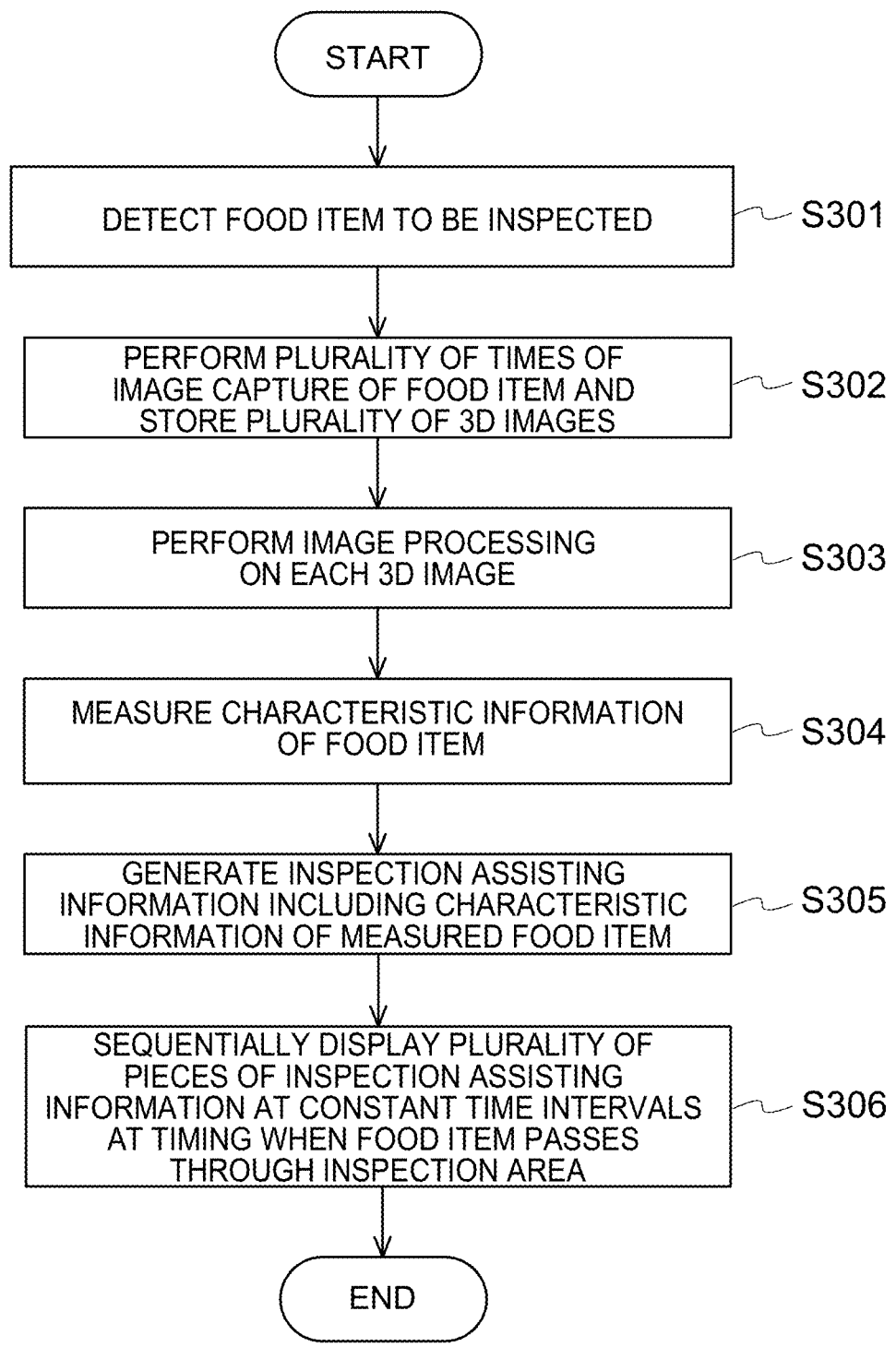
FIG. 19 is a flowchart of an example of operations according to the fourth embodiment.

FIG. 19 is a flowchart of an example of operations according to the embodiment of the present invention. When the sensor 23 detects that a food item to be inspected enters the image-capturing region of the image capturing apparatus 2 (step S301), the sensor 23 sends a detection signal to the controller 13. The controller 13 outputs a signal for instruction of image capture to the 3D camera 112. The 3D camera 112 performs a plurality of times of image capture (continuous image capture) at constant time intervals, and the controller 13 stores the plurality of captured images (3D images) in the image storage 11 (S302). The image processor 12 performs image processing (processing of reducing noise components) on each captured image (S303).

The detection processor 14 measures characteristic information of the food item based on the processed image (S304). For example, the detection processor 14 measures at least one of the weight, size and fat proportion of the food item.

The assisting information generator 15 generates inspection assisting information including the measured characteristic information (S305).

The controller 13 receives the plurality of pieces of inspection assisting information generated for the plurality of captured images, and sequentially outputs the plurality of pieces of inspection assisting information to the projector 71 at constant time intervals at the timing when the food item to be inspected is carried in the inspection area (S306). The projector 71 projects the plurality of pieces of inspection assisting information at constant time intervals (also S306). This allows the position of the characteristic information included in the projected inspection assisting information to be moved in accordance with the movement of the food item on the carrying channel, so that the characteristic information is projected on the food item in accordance with the movement of the food item being carried. The worker can continue checking the information (such as weight information) projected on the food item without interruption. The various extended examples and modified examples described in the third embodiment are also applicable to the present embodiment.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

REFERENCE SIGNS LIST 1 food inspection assisting apparatus
2 image capturing apparatus
3 display
4 conveying apparatus
4a collecting apparatus
5 frame data
11 image storage
12 image processor
13 controller
14 detection processor
15 assisting information generator
21, 122, 121 chicken (food)
21a foreign matter (feather)
23, 24 sensor
27 worker
28 arm member
30 region
31, 52 lighting unit
32, 55 camera
33 filter
34, 54 opening
53, 56 polarizing plate
71 projector
82 projection region
111 measurement processor
112 3D camera

The invention claimed is:

1. A food inspection assisting apparatus comprising:
a first circuitry configured to acquire a captured image of a food item being carried by a conveyor from a first sensor irradiating the food item with ultraviolet light and detecting generated fluorescence through a green filter, generate a binary image based on the image captured through the green filter, and detect a foreign matter or defect included in the food item based on the binary image;
a second circuitry configured to generate an inspection assisting information for the food item based on the captured image, wherein the inspection assisting information includes an information identifying a position of the detected foreign matter or a position of the detected defect; and
a third circuitry configured to control display timing of the inspection assisting information to be displayed by an information output device based on time required to convey the food item to an inspection area in which the food item is inspected.

2. The food inspection assisting apparatus according to claim 1, wherein the second circuitry is further configured to generate an indicating data of a position of the detected foreign matter or the detected defect, and generate the inspection assisting information including an image in which the indicating data is arranged at the position of the detected foreign matter or the detected defect.

3. A food inspection assisting system comprising:
the food inspection assisting apparatus according to claim 1;
the conveyer configured to carry the food item on a carrying surface to the inspection area; and
the information output device which includes a fourth circuitry configured to display the inspection assisting information;
wherein the third circuitry is further configured to move a position of displaying the inspection assisting information in synchronization with movement of the food item carried in the inspection area.

4. A food inspection assisting system comprising:
the food inspection assisting apparatus according to claim 1;
the conveyer configured to carry the food item on a carrying surface to the inspection area; and
the information output device which comprises a display that displays the inspection assisting information on a screen, or a projector that projects the inspection assisting information to a carrying channel in the inspection area or to the food item carried in the inspection area.

5. A food inspection assisting system comprising:
the food inspection assisting apparatus according to claim 1;
the conveyer configured to carry the food item on a carrying surface to the inspection area;
the information output device configured to display the inspection assisting information; and
a second sensor that detects a passage of the food item,
wherein the third circuitry is further configured to perform control to display the inspection assisting information when the food item is detected by the second sensor.

6. A food inspection assisting apparatus comprising:
a first circuitry configured to acquire a color image of a food item from a first sensor capturing an image of the food item being carried by a conveyor, generates a difference image between a red image and a green image included in the color image, and detects a foreign matter or defect included in the food item based on the difference image;
a second circuitry configured to generate an inspection assisting information for the food item based on the captured image, the inspection assisting information includes an information identifying a position of the detected foreign matter or a position of the detected defect; and
a third circuitry configured to control display timing of the inspection assisting information to be displayed by an information output device based on time required to convey the food item to an inspection area in which the food item is inspected.

7. The food inspection assisting apparatus according to claim 6, wherein the second circuitry is further configured to generate an indicating data of a position of the detected foreign matter or the detected defect, and generate the inspection assisting information including an image in which the indicating data is arranged at the position of the detected foreign matter or the detected defect.

8. A food inspection assisting system comprising:
the food inspection assisting apparatus according to claim 6;
the conveyer configured to carry the food item on a carrying surface to the inspection area; and
the information output device which includes a fourth circuitry configured to display the inspection assisting information;
wherein the third circuitry is further configured to move a position of displaying the inspection assisting information in synchronization with movement of the food item carried in the inspection area.

9. A food inspection assisting system comprising:
the food inspection assisting apparatus according to claim 6;
the conveyer configured to carry the food item on a carrying surface to the inspection area; and
the information output device which comprises a display that displays the inspection assisting information on a screen, or a projector that projects the inspection assisting information to a carrying channel in the inspection area or to the food item carried in the inspection area.

10. A food inspection assisting system comprising:
the food inspection assisting apparatus according to claim 6;
the conveyer configured to carry the food item on a carrying surface to the inspection area;
the information output device configured to display the inspection assisting information; and
a second sensor that detects a passage of the food item, wherein the third circuitry is further configured to perform control to display the inspection assisting information when the food item is detected by the second sensor.

11. A food inspection assisting apparatus comprising:
a first circuitry configured to acquire an infrared image and a color image of a food item from a first sensor capturing an image of the food item being carried by a conveyor, generates a difference image between the infrared image and a green image included in the color image, and detects a foreign matter or defect included in the food item based on the difference image;
a second circuitry configured to generate an inspection assisting information for the food item based on the captured image, wherein the inspection assisting information includes an information identifying a position of the detected foreign matter or a position of the detected defect; and
a third circuitry configured to control display timing of the inspection assisting information to be displayed by an information output device based on time required to convey the food item to an inspection area in which the food item is inspected.

12. The food inspection assisting apparatus according to claim 11, wherein the second circuitry is further configured to generate an indicating data of a position of the detected foreign matter or the detected defect, and generate the inspection assisting information including an image in which the indicating data is arranged at the position of the detected foreign matter or the detected defect.

13. A food inspection assisting system comprising:
the food inspection assisting apparatus according to claim 11;
the conveyer configured to carry the food item on a carrying surface to the inspection area; and
the information output device which includes a fourth circuitry configured to display the inspection assisting information;
wherein the third circuitry is further configured to move a position of displaying the inspection assisting information in synchronization with movement of the food item carried in the inspection area.

14. A food inspection assisting system comprising:
the food inspection assisting apparatus according to claim 11;
the conveyer configured to carry the food item on a carrying surface to the inspection area; and
the information output device which comprises a display configured to display the inspection assisting information on a screen, or a projector configured to project the inspection assisting information to a carrying channel in the inspection area or to the food item carried in the inspection area.

15. A food inspection assisting system comprising:
the food inspection assisting apparatus according to claim 11;
the conveyer configured to carry the food item on a carrying surface to the inspection area;
the information output device configured to display the inspection assisting information; and
a second sensor that detects a passage of the food item, wherein the third circuitry is further configured to perform control to display the inspection assisting information when the food item is detected by the second sensor.

16. A food inspection assisting apparatus comprising:
a first circuitry configured to acquire a plurality of continuously captured images from a first sensor continuously capturing images of a food item being carried by a conveyor, and generate a plurality of inspection assisting information for the food item based on the plurality of captured images;
a second circuitry configured to control display timing of the plurality of inspection assisting information to be displayed by an information output device based on time required to convey the food item to an inspection area in which the food item is inspected;
the conveyer configured to carry the food item on a carrying surface to the inspection area; and
the information output device which comprises a display that displays the inspection assisting information on a screen, or a projector that projects the inspection assisting information to a carrying channel in the inspection area or to the food item carried in the inspection area,
wherein the second circuitry is further configured to control to continuously display the plurality of inspection assisting information obtained in correspondence with the plurality of captured images.

17. The food inspection assisting apparatus according to claim 16,
wherein the second circuitry is further configured to move a position of displaying the inspection assisting information in synchronization with movement of the food item carried in the inspection area.

18. The food inspection assisting apparatus according to claim 16, further comprising a third circuitry that detects a foreign matter or a defect from the captured image of the first sensor,
wherein the first circuitry is further configured to generate an indicating data of a position of the detected foreign matter or the detected defect, and generate the inspection assisting information including an image in which the indicating data is arranged at the position of the detected foreign matter or the detected defect.

19. The food inspection assisting apparatus according to claim 16, further comprising a second sensor that detects a passage of the food item,
wherein the second circuitry is further configured to perform control to display the inspection assisting information when the food item is detected by the second sensor.

* * * * *